United States Patent [19]
Sato et al.

[11] Patent Number: 4,721,667
[45] Date of Patent: Jan. 26, 1988

[54] COLOR LIGHT-SENSITIVE MATERIAL

[75] Inventors: Kozo Sato; Tadahisa Sato; Takeshi Shibata, all of Kanagawa, Japan

[73] Assignee: Fuji Photo Film Co., Ltd., Kanagawa, Japan

[21] Appl. No.: 864,061

[22] Filed: May 16, 1986

[30] Foreign Application Priority Data

May 16, 1985 [JP] Japan .................. 60-102730

[51] Int. Cl.$^4$ .................. G03C 1/40; G03C 5/54; G03C 7/26
[52] U.S. Cl. .................. 430/562; 430/222; 430/223; 430/559
[58] Field of Search .................. 430/223, 224, 225, 562, 430/222, 226, 559

[56] References Cited

U.S. PATENT DOCUMENTS 4,183,753  1/1980  Baigrie et al. .................. 430/223
4,461,827  7/1984  Bergthaller et al. .................. 430/223
4,607,003  8/1986  Ukai et al. .................. 430/519

Primary Examiner—Richard L. Schilling
Attorney, Agent, or Firm—Sughrue, Mion, Zinn, Macpeak & Seas

[57] ABSTRACT

A color light-sensitive material is provided, having at least one image forming compound of the following formula (I) on support.

$$(\text{Dye-X})_q\text{-Y} \quad (\text{I})$$

wherein Dye represents a yellow dye residue represented by the following formula (II) or a dye precursor residue; X represents a bond or a binding group; Y represents a group capable of yielding a difference of diffusibility of a dye component before and after the reaction with a photographic silver salt imagewise having a latent image, corresponding to or reversely corresponding to said photographic silver salt; q is 1 or 2, and when q is 2, Dye-X may be the same or different;

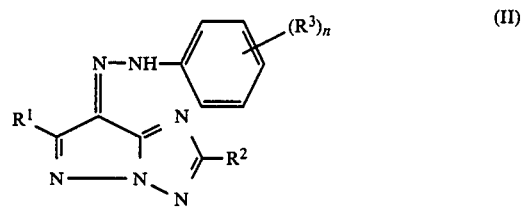

wherein $R^1$, $R^2$ and $R^3$ may be the same or different and each represents a group selected from a hydrogen atom, a halogen atom, a hydroxyl group, a cyano group, a carboxyl group, or a substituted or unsubstituted alkyl, aralkyl, cycloalkyl, aryl, heterocyclic, alkoxy, aryloxy, amino, acylamino, sulfonylamino, acyl, sulfonyl, carbamoyl, sulfamoyl, ureido, alkylthio or arylthio group; n is an integer of 2 to 4, $R^3$ may be the same or different; Dye and X are bound to each other via any of said $R^1$, $R^2$ and $R^3$ in the formula (II).

20 Claims, No Drawings

COLOR LIGHT-SENSITIVE MATERIAL

FIELD OF THE INVENTION

The present invention relates to new yellow azo color image forming compounds and color light-sensitive materials containing said compound.

BACKGROUND OF THE INVENTION

A color diffusion transfer photography has heretofore been well known, using an azo color image forming compound which may form an azo dye having a diffusibility different from that of said image forming compound itself as a result of development under a basic condition. For instance, image forming compounds capable of releasing a yellow dye are known, for example, as described in Japanese Patent Application (OPI) Nos. 7727/77 and 79031/79 (the term "OPI" as used herein refers to a "published unexamined Japanese patent application") and U.S. Pat. No. 4,473,632.

However, the compounds as described in said publications contain as a coupling component 1-aryl-5-pyrazolones or electron attractive group-containing phenols and, therefore, these have low dye transferring ability and low light fastness. In addition, the yield in the azo dye forming step by the coupling reaction is low. Thus, said known compounds have various defects.

SUMMARY OF THE INVENTION

The first object of the present invention is to provide compounds capable of forming an image of high density in a short period of time for transfer.

The second object of the present invention is to provide compounds capable of forming an image of high light fastness.

The third object of the present invention is to provide color light-sensitive materials containing said compound.

The present inventors have investigated various problems and, as a result, have found that a color photographic material containing at least one azo color image forming compound of the following formula (I) can effectively satisfy the above-mentioned objects and can overcome the above-mentioned defects in the prior art and, therefore, can attain sufficiently satisfactory photographic characteristics in this technical field.

$$(\text{Dye-X})_q\text{—Y} \quad (I)$$

wherein Dye represents a yellow dye residue or a dye precursor residue represented by the following formula (II); X represents a bond or a binding group; Y represents a group capable of yielding a difference of diffusibility of a dye component before and after the reaction with a photographic silver salt imagewise having a latent image, corresponding to or reversely corresponding to said photographic silver salt; q is 1 or 2, and when q is 2, Dye-X may be the same or different;

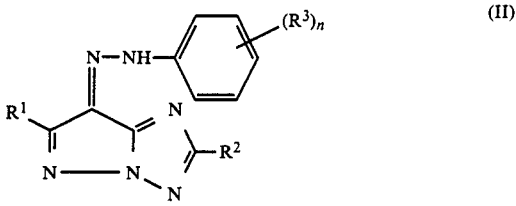

wherein $R^1$, $R^2$ and $R^3$ may be the same or different and each represents a group selected from a hydrogen atom, a halogen atom, a hydroxyl group, a cyano group, a carboxyl group, a substituted or unsubstituted alkyl, aralkyl, cycloalkyl, aryl, heterocyclic, alkoxy, aryloxy, amino, acylamino, sulfonylamino, acyl, sulfonyl, carbamoyl, sulfamoyl, ureido, alkylthio or arylthio group; n is an integer selected from 0 to 4, and when n is an integer of from 2 to 4, said $R^3$ may be the same or different; Dye and X are bound to each other via any of said $R^1$, $R^2$ and $R^3$ in the formula (II).

DETAILED DESCRIPTION OF THE INVENTION

X may represent a binding group, including an —$NR^4$— group (in which $R^4$ represents a hydrogen atom, an alkyl group or a substituted alkyl group), an —$SO_2$— group, a —CO— group, an alkylene group, a substituted alkylene group, a phenylene group, a substituted phenylene group, a naphthylene group, a substituted naphthylene group, an —O— group, an —SO— group or a group formed by the combination of two or more of said groups. Preferred binding groups among them are —$NR^4$—$SO_2$—, —$NR^4$—CO— or —$R^5$—$(L)_k(R^6)_l$, in which $R^5$ and $R^6$ each represents an alkylene group, a substituted alkylene group, a phenylene group, a substituted phenylene group, a naphthylene group or a substituted naphthylene group, L represents —O—, —CO—, —SO—, —$SO_2$—, —$SO_2NH$—, —$NHSO_2$—, —CONH— or —NHCO—, k is 0 or 1, l is 1 when k=1, and l is 0 or 1 when k=0.

A combination comprising —$NR^4$—$SO_2$— and —$NR^4$—CO— or —$R^5$—$(L)_k(R^6)_l$ is especially preferred.

The color photographic materials of the present invention preferably contain a light-sensitive silver salt, more preferably a light-sensitive silver halide, and said salt is preferably incorporated in the same layer containing the compound of formula (I).

Preferred examples of $R^1$ in the formula (II) are a substituted or unsubstituted alkyl group having from 1 to 4 carbon atoms (such as a methyl group, an isopropyl group, a t-butyl group, a methoxyethyl group, a β-cyanoethyl group, a trifluoromethyl group, etc.), a substituted or unsubstituted alkoxy group having from 1 to 4 carbon atoms (such as a methoxy group, an ethoxy group, a methoxyethoxy group, etc.), a substituted or unsubstituted aryl group having from 6 to 8 carbon atoms (such as a phenyl group, a p-methoxyphenyl group, a p-hydroxyphenyl group, etc.), a hydroxyl group, a cyano group, a carbamoyl group or a carboxyl group. Preferred examples of $R^2$ in the formula (II) are a substituted or unsubstituted alkyl group having from 1 to 8 carbon atoms (such as a methyl group, a butyl group, a methoxyethyl group, a β-cyanoethyl group, a β-acetylaminoethyl group, a β-methanesulfonylaminoethyl group, etc.), a substituted or unsubstituted aryl group having from 6 to 8 carbon atoms (such as a phenyl group, a p-methoxyphenyl group, a p-chlorophenyl group, etc.), a substituted or unsubstituted aralkyl group having from 7 to 12 carbon atoms (such as benzyl group, a β-phenethyl group, a p-methoxyphenethyl group, etc.), a substituted or unsubstituted alkoxy group having from 1 to 6 carbon atoms (such as a methoxy group, an ethoxy group, a methoxyethoxy group, etc.), an acylamino group having from 2 to 8 carbon atoms (such as an acetylamino group, a butyroylamino group, a pivaloylamino group, etc.), or a sulfonylamino group having from 1 to 7 carbon atoms (such as a methanesulfonylamino group, a benzenesulfonylamino group, etc.). Preferred examples of $R^3$ in the formula (II) are a hydrogen atom, a halogen atom, a cyano group, a carboxyl group, a substituted or unsubstituted carbamoyl group having from 1 to 5 carbon atoms (such as a carbamoyl group, an N-methylcarbamoyl group, an N,N-dimethylcarbamoyl group, etc.), a substituted or unsubstituted sulfamoyl group having from 0 to 4 carbon atoms (such as a sulfamoyl group, an N-methylsulfamoyl group, an N,N-dimethylsulfamoyl group, etc.), a substituted or unsubstituted sulfonyl group having from 1 to 4 carbon atoms (such as a methanesulfonyl group, an ethanesulfonyl group, etc.), a methyl group, a methoxy group or a methoxyethoxy group. Dye and X are bound to each other via any of $R^1$, $R^2$ and $R^3$, especially preferably via $R^2$ or $R^3$. n in the formula (II) is an integer of from 0 to 4, and when n is from 2 to 4, said $R^3$ may be the same or different.

Next, Y is explained in detail hereunder.

Y is first so selected that the compound of the formula (I) is a nondiffusible image forming compound capable of being oxidized to self-cleave, after developed, thereby to yield a diffusible dye.

One example of Y which is effective for said type of compounds is an N-substituted sulfamoyl group. For instance, Y represents a group of the following formula $(Y_I)$:

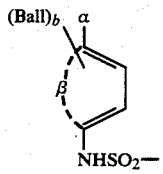

wherein β represents a non-metallic atomic group necessary for formation of a benzene ring, which may be condensed with a carbon ring or a hetero ring, for example, to form a naphthalene ring, a quinoline ring, a 5,6,7,8-tetrahydronaphthalene ring or a chroman ring.

α represents $-OG^{11}$ or $-NHG^{12}$, in which $G^{11}$ represents a hydrogen atom or a group capable of being hydrolyzed to form a hydroxyl group, and $G^{12}$ represents a hydrogen atom, an alkyl group having from 1 to 22 carbon atoms or a group which makes said $NHG^{12}$ hydrolyzable. Ball represents a ballast group; and b is 0, 1 or 2.

Examples of Y are described in Japanese Patent Application (OPI) Nos. 33826/73 and 50736/78.

Another example of Y which is suitable for said type of compounds is a group represented by the following formula $(Y_{II})$:

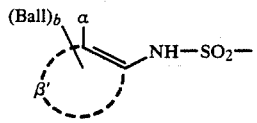

wherein Ball, α and b have the same meanings as in the formula $(Y_I)$; β' represents an atomic group necessary for formation of a carbon ring such as a benzene ring, which may further be condensed with a carbon ring or a hetero ring, for example, to form a naphthalene ring, a quinoline ring, a 5,6,7,8-tetrahydronaphthalene ring or a chroman ring.

Examples of said kind of Y are described in Japanese Patent Application (OPI) Nos. 113624/76, 12642/81, 16130/81, 16131/81, 4043/82 and 650/82 and U.S. Pat. No. 4,053,312.

Still another example of Y which is suitable for said type of compounds is a group represented by the following formula $(Y_{III})$:

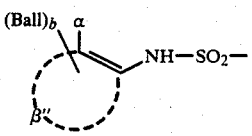

wherein Ball, α and b have the same meanings as in the formula $(Y_I)$; and β" represents an atomic group necessary for formation of a hetero ring such as a pyrazole ring or a pyridine ring, which may further be condensed with a carbon ring or a hetero ring. Examples of said kind of Y are described in Japanese Patent Application (OPI) No. 104343/76.

A further example of Y which is effective for said type of compounds is a group represented by the following formula $(Y_{IV})$:

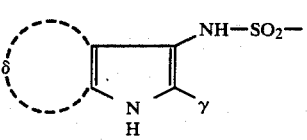

wherein γ preferably represents a hydrogen atom or a substituted or unsubstituted alkyl, aryl or heterocyclic group, or a group of $-CO-G^{21}$, $G^{21}$ represents a group of

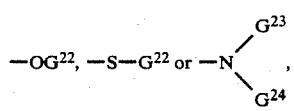

$G^{22}$ represents a hydrogen atom, an alkyl group, a cycloalkyl group or an aryl group, $G^{23}$ represents the same group as $G^{22}$ or represents an acyl group derived from an aliphatic or aromatic carboxylic or sulfonic acid, $G^{24}$ represents a hydrogen atom or a substituted or unsubstituted alkyl group; δ represents a residue necessary for completing a condensed benzene ring.

Examples of said kind of Y are described in Japanese Patent Application (OPI) Nos. 104343/76, 46730/78, 130122/79 and 85055/82.

A further example of Y which is suitable for said type of compounds is a group represented by the following formula (Y$_V$):

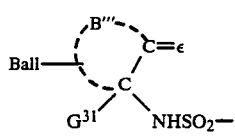

(Y$_V$)

wherein Ball has the same meaning as in the formula (Y$_I$); ε represents an oxygen atom or =NG$^{32}$ (where G$^{32}$ represents a hydroxyl group or an optionally substituted amino group), examples of compounds of H$_2$N-G$^{32}$ are, for example, hydroxylamines, hydrazines, semicarbazides and thiosemicarbazides; β''' represents an atomic group necessary for formation of a 5-, 6- or 7-membered, saturated or unsaturated nonaromatic hydrocarbon ring; G$^{31}$ represents a hydrogen atom or a halogen atom such as a fluorine, chlorine or bromine atom. Examples of said kind of Y are described in Japanese Patent Application (OPI) Nos. 3819/78 and 48534/79.

Other examples of Y of said type of compounds are those as described in Japanese Patent Publication Nos. 32129/73 and 39165/73, Japanese Patent Application (OPI) No. 64436/74 and U.S. Pat. No. 3,434,934.

Still further examples of Y in the present invention are those represented by the following formula (Y$_{VI}$):

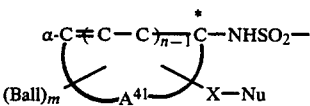

(Y$_{VI}$)

wherein α represents OR$^{41}$ or NHR$^{42}$, R$^{41}$ represents a hydrogen atom or a hydrolyzable component residue, R$^{42}$ represents a hydrogen atom or an alkyl group having from 1 to 50 carbon atoms or represents a group which makes NHR$^{42}$ hydrolyzable; A$^{41}$ represents an atomic group necessary for formation of an aromatic ring; Ball represents an organic group which may keep the compound in a passive state, as existing in an aromatic ring, and plural Ball's may be the same or different; m is an integer of 1 or 2; X represents a divalent organic group having from 1 to 8 carbon atoms; a nucleophilic group (Nu) and an electrophilic center (asterisked carbon, C*) formed by oxidation form a 5-membered to 12-membered ring; Nu represents a nucleophilic group; and n is an integer of 1 or 2.

Examples of said kind of Y are described in Japanese Patent Application (OPI) No. 20735/82.

Another type of compound falling within the scope of the formula (I) is a nondiffusible image forming compound which may release a diffusible dye after self ring closure under basic conditions but does not substantially release any dye when reacted with an oxidized form of a developing agent.

One example of Y which is effective for said type of compounds is a group of the following formula (Y$_{VII}$):

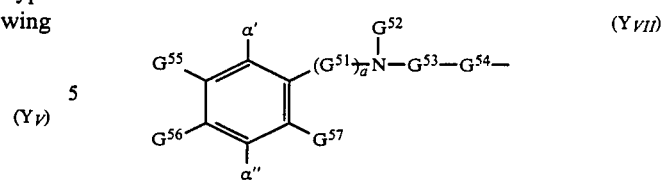

(Y$_{VII}$)

wherein α' represents an oxidizable nucleophilic group such as a hydroxyl group, a primary or secondary amino group, a hydroxylamino group or a sulfonamido group, or a precursor thereof; α'' represents a dialkylamino group or may be any group as defined in α'; G$^{51}$ represents an alkylene group having from 1 to 3 carbon atoms; a is 0 or 1; G$^{52}$ represents a substituted or unsubstituted alkyl group having from 1 to 40 carbon atoms or a substituted or unsubstituted aryl group having from 6 to 40 carbon atoms; G$^{53}$ represents an electrophilic group such as —CO— or —CS—; G$^{54}$ represents an oxygen atom, a sulfur atom, a selenium atom or a nitrogen atom, and when this is a nitrogen atom, said nitrogen atom may be substituted with a hydrogen atom, an alkyl or substituted alkyl group having from 1 to 10 carbon atoms or an aromatic residue having from 6 to 20 carbon atoms; G$^{55}$, G$^{56}$ and G$^{57}$ each represents a hydrogen atom, a halogen atom, a carbonyl group, a sulfamyl group, a sulfonamido group or an alkyloxy group having from 1 to 40 carbon atoms, or may have the same meaning as the group G$^{52}$, G$^{55}$ and G$^{56}$ may together form a 5-membered to 7-membered ring, or G$^{56}$ may represent a group of

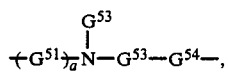

with the proviso that at least one of G$^{52}$, G$^{55}$, G$^{56}$ and G$^{57}$ must represent a ballast group.

Examples of said kind of Y are described in Japanese Patent Application (OPI) No. 63618/76.

Other examples of Y which are suitable for said type of compounds are those of the following formulae (Y$_{VIII}$) and (Y$_{IX}$):

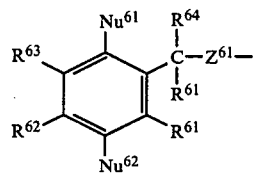

(Y$_{VIII}$)

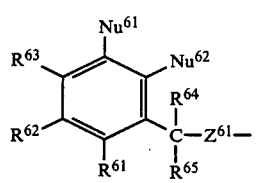

(Y$_{IX}$)

In the above formulae, Nu$^{61}$ and Nu$^{62}$ may be the same or different and each represents a nucleophilic group or a precurosr thereof; Z$^{61}$ represents a divalent atomic group which is electrically negative to the carbon atom substituted by groups R$^{64}$ and R$^{65}$; R$^{61}$, R$^{62}$ and R$^{63}$ each represents a hydrogen atom, a halogen atom, an alkyl group, an alkoxy group or an acylamino group, or $R^{61}$ and $R^{62}$ may form a condensed ring, when positioned in the adjacent positions on the ring, together with the remaining atoms of the molecule, or $R^{62}$ and $R^{63}$ may form a condensed ring together with the remaining atoms of the molecule; $R^{64}$ and $R^{65}$ may be the same or different and each represents a hydrogen atom, a hydrocarbon residue or a substituted hydrocarbon residue, with the proviso that at least one of said substituents $R^{61}$, $R^{62}$, $R^{63}$, $R^{64}$ and $R^{65}$ must contain a ballast group (Ball) of a sufficiently large size so that said compound may be kept to be immobile.

Examples of said kind of Y are described in Japanese Patent Application (OPI) Nos. 69033/78 and 130927/79.

Still another example of Y which is suitable for said type of compounds is a group represented by the following formula ($Y_X$):

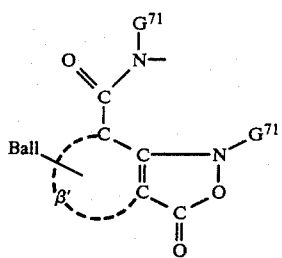

wherein Ball and $\beta'$ have the same meanings as in the formula ($Y_{II}$); and $G^{71}$ represents an alkyl group (including a substituted alkyl group). Examples of said kind of Y are described in Japanese Patent Application (OPI) Nos. 111628/74 and 4819/77.

Still another type of compound falling in the scope of the formula (I) is a nondiffusible image forming compound which itself does not release any dye but may release, when reacted with a reducing agent, a dye. In the case when this type of compound is used in the present invention, it is preferred to co-use a compound capable of mediating a redox reaction (or a so-called electron donor) together with said compound.

One example of Y which is effective for said type of compounds is a group of the following formula ($Y_{XI}$):

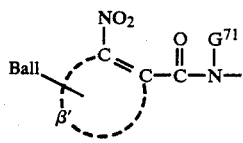

wherein Ball and $\beta'$ have the same meanings as in the formula ($Y_{II}$); and $G^{71}$ represents an alkyl group (including a substituted alkyl group). Examples of said kind of Y are described in Japanese Patent Application (OPI) Nos. 35533/78 and 110827/78.

Another example of Y which is suitable for said type of compounds is a group of the following formula ($Y_{XII}$):

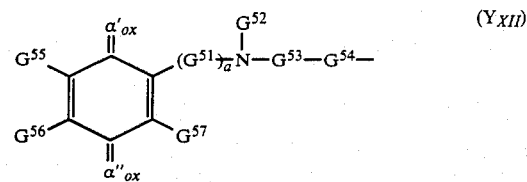

wherein $\alpha'_{ox}$ and $\alpha''_{ox}$ each represents a group capable of yielding a group of $\alpha'$ or $\alpha''$, respectively, by reduction; $\alpha'$, $\alpha''$, $G^{51}$, $G^{52}$, $G^{53}$, $G^{54}$, $G^{55}$, $G^{56}$, $G^{57}$ and a have the same meanings as in the formula ($Y_{VII}$).

Examples of said kind of Y are described in Japanese Patent Application (OPI) No. 110827/78 and U.S. Pat. Nos. 4,356,249 and 4,358,525.

Other examples of Y which are suitable for said type of compounds are those represented by the following formulae ($Y_{XIIIA}$) and ($Y_{XIIIB}$):

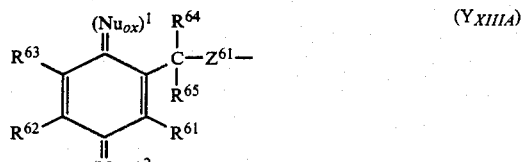

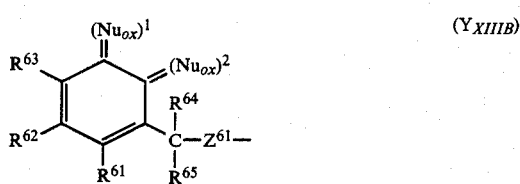

In the above formulae, $(Nu_{ox})^1$ and $(Nu_{ox})^2$ may be the same or different and each represents an oxidized nucleophilic group; and the other symbols have the same meaning as in the formulae ($Y_{VIII}$) and ($Y_{IX}$). Examples of said kind of Y are described in Japanese Patent Application (OPI) Nos. 130927/79 and 164342/81.

In the related patent specifications as referred to with respect to the groups of ($Y_{XI}$), ($Y_{XII}$), ($Y_{XIIIA}$) and ($Y_{XIIIB}$), various electron donors which may be co-used together with the compounds of the present invention are described.

Still another type of compound falling within the scope of the formula (I) is an LDA compound (Linked Donor Acceptor compound). This compound is a nondiffusible image forming compound which may release a diffusible dye, after reacted by a donor acceptor reaction in the presence of a base, but does not substantially release any dye when reacted with an oxidized form of a developing agent.

Examples of Y which are effective for said type of compounds are those represented by the following formula ($Y_{XIV}$). Concrete examples of Y are described in Japanese Patent Application (OPI) No. 60289/83.

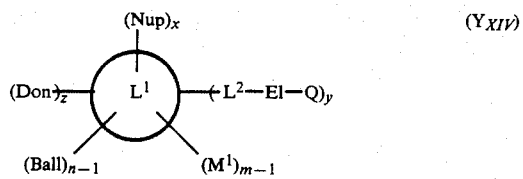

wherein n, x, y and z each is 1 or 2; m is an integer of 1 or more; Don represents an electron donor or a precursor-containing residue; $L^1$ represents an organic group for binding Nup and $-L^2-El-Q$, etc.; Nup represents a precursor of a nucleophilic group; El represents an electrophilic center; Q represents a divalent group; Ball represents a ballast group; $L^2$ represents a binding group; $M^1$ represents a substituent.

The ballast groups in the above formulae ($Y_I$) through ($Y_{XIV}$) are an organic ballast group which may make the color image forming compounds of the formula (I) nondiffusible, and are preferably a group which contains a hydrophobic group having from 8 to 32 carbon atoms. Said organic ballast group is bonded to the color image forming compound of the formula (I) directly or via a binding group (such as an imino bond, an ether bond, a thioether bond, a carbonamido bond, a sulfonamido bond, a ureido bond, an ester bond, a carbamoyl bond or a sulfamonyl bond or a combination thereof).

The image forming compound of the present invention is used in an amount of from 0.01 to 4 mol per mol of silver.

Examples of image forming compounds which are preferably used in the present invention are given hereunder.

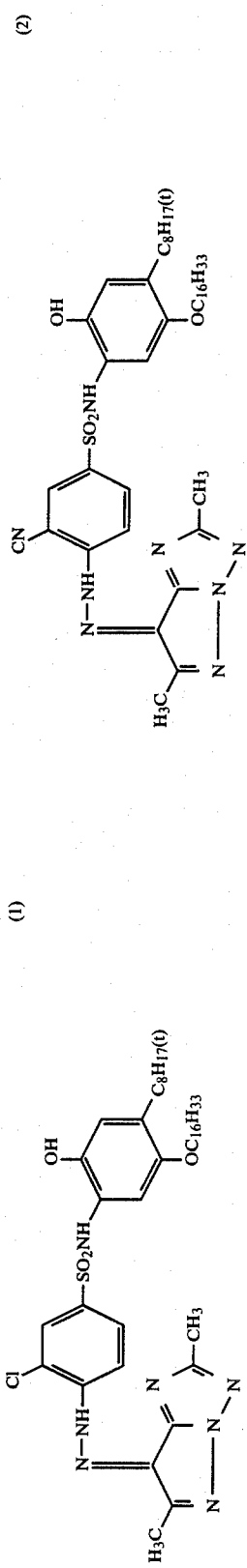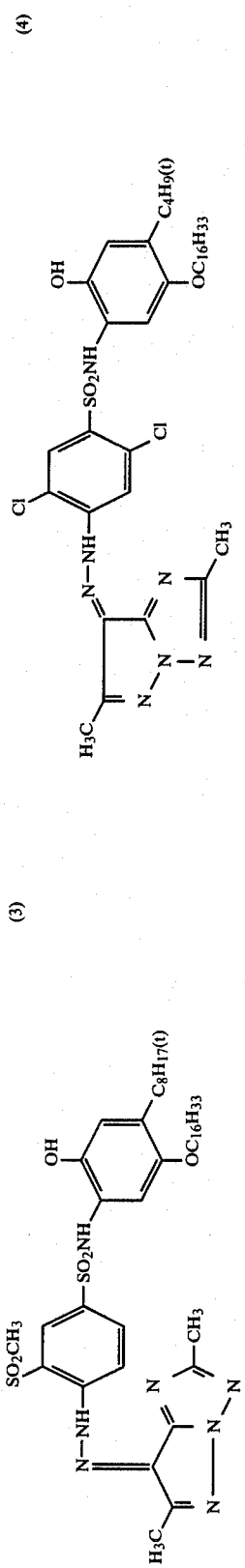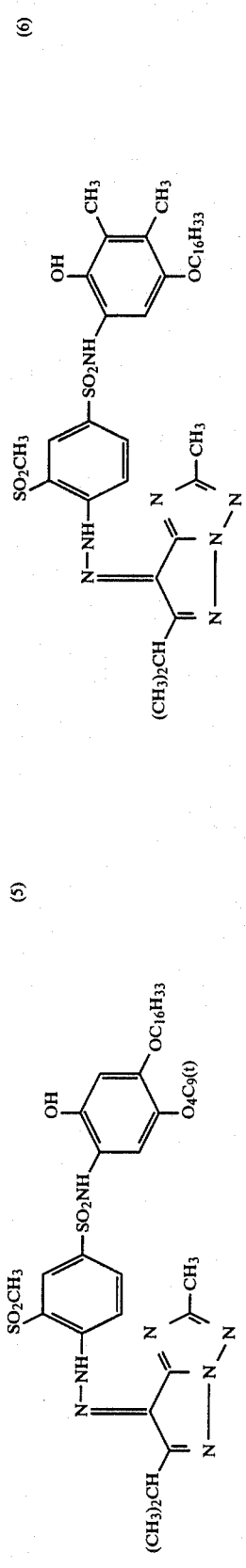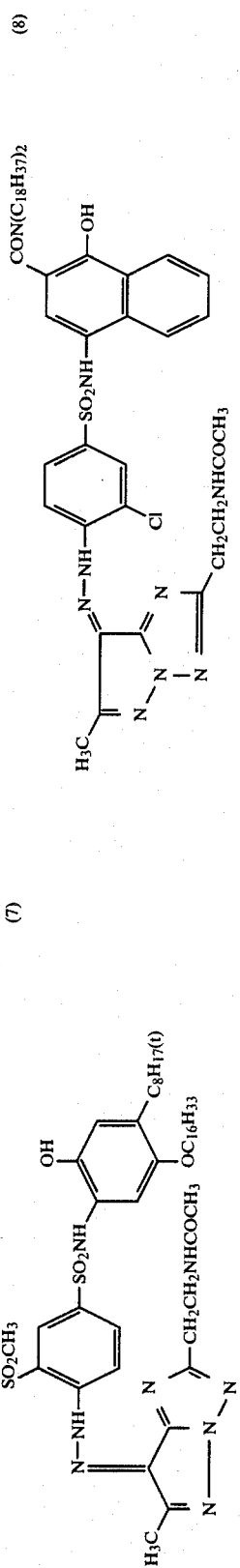

-continued
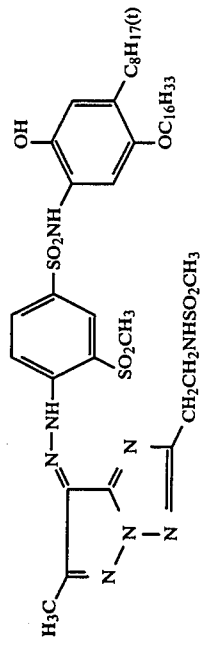
(9)
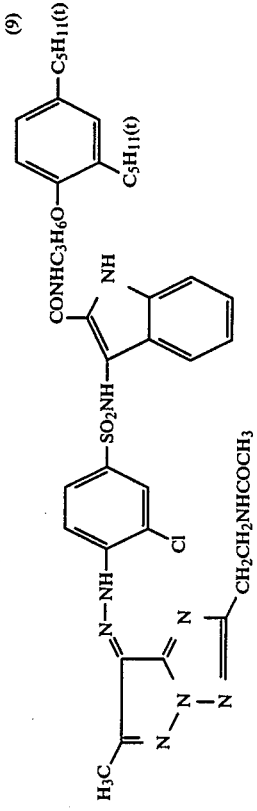
(10)
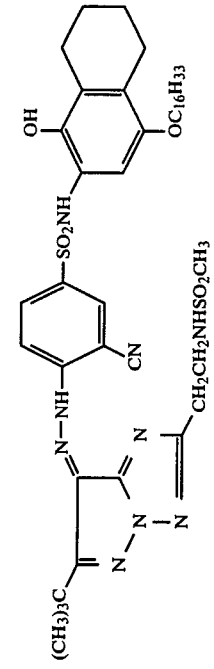
(11)
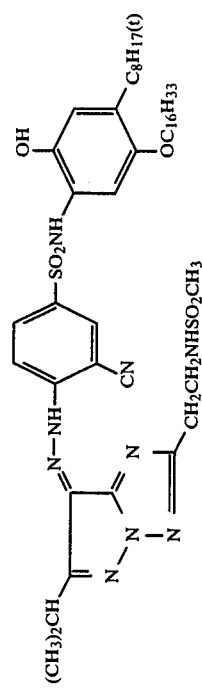
(12)
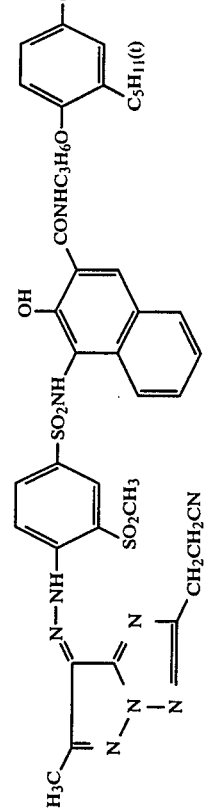
(13)
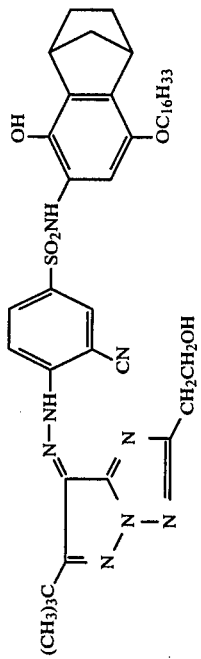
(14)
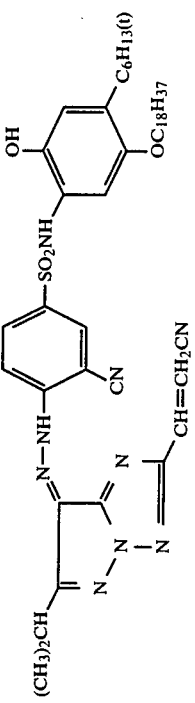
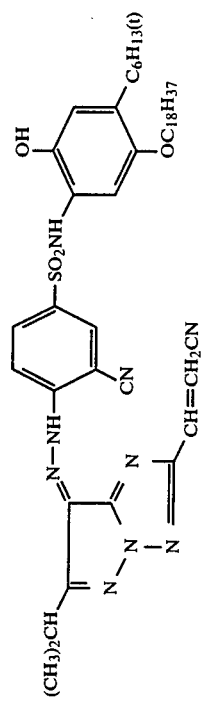
(15)

-continued
(16) 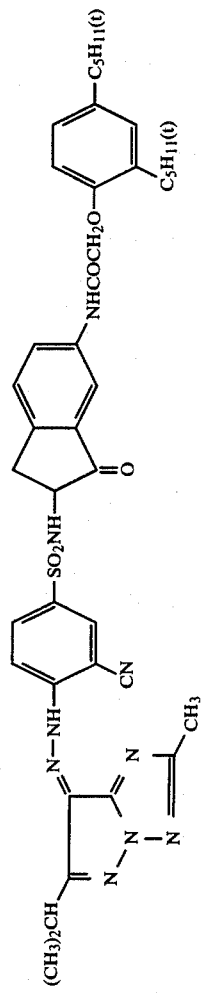
(17) 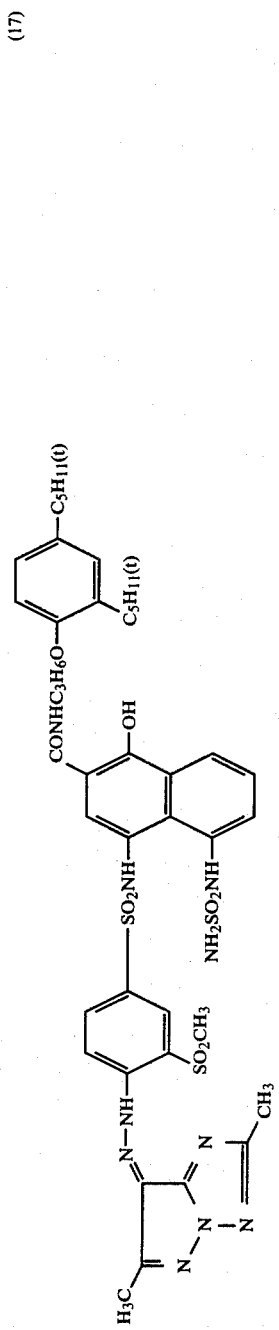
(18) 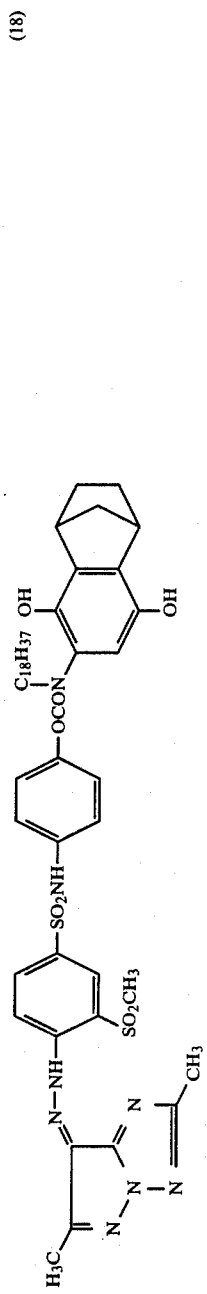
(20) 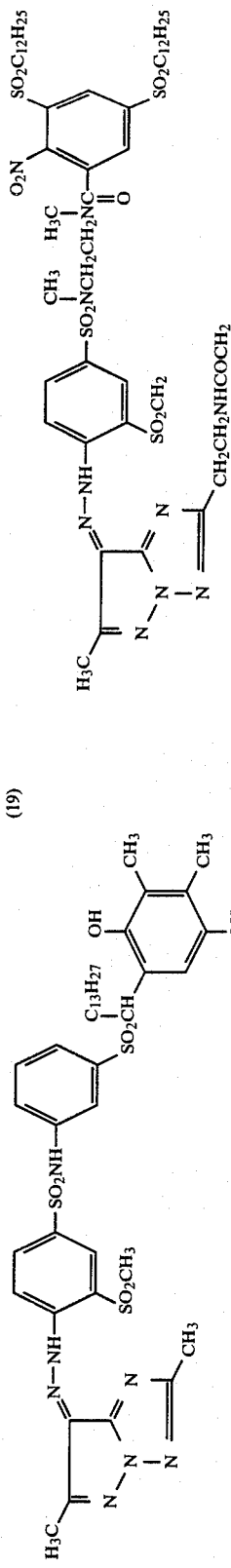
(19) 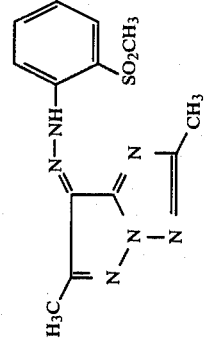

-continued
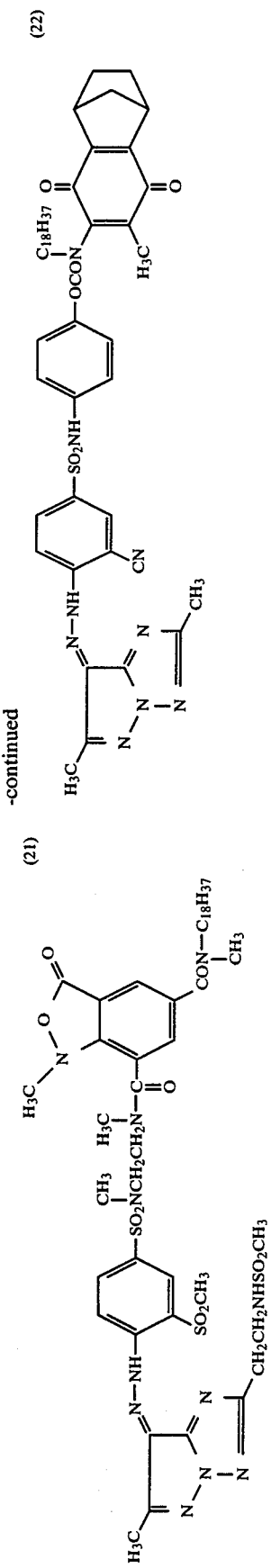
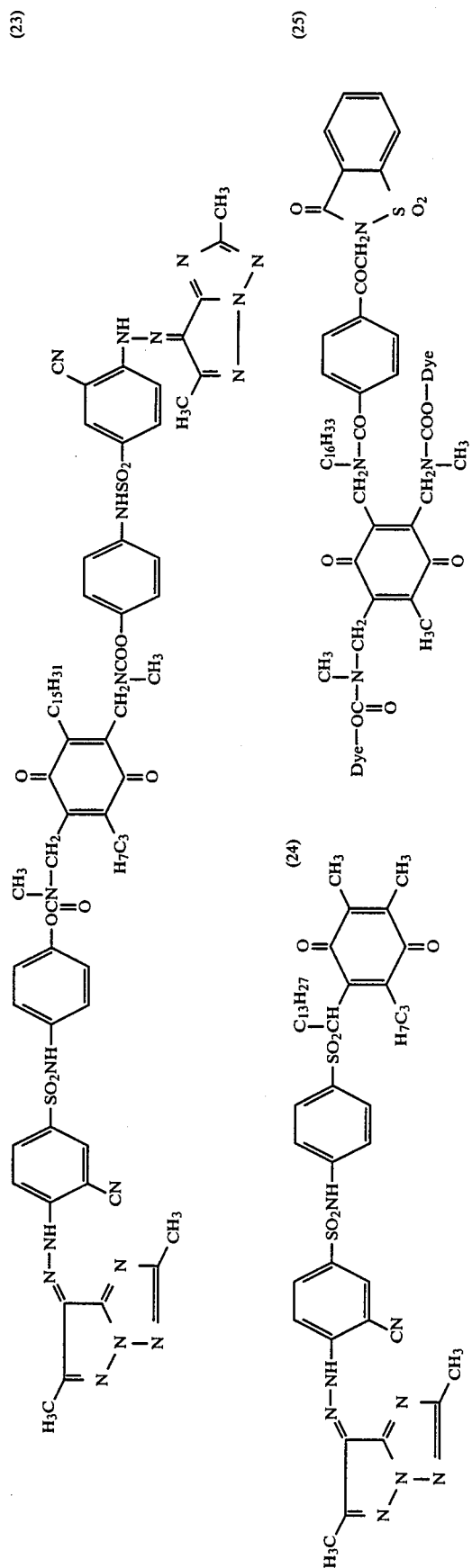

wherein Dye is:

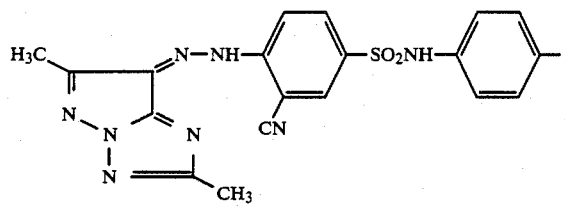

Next, the synthesis of image forming compounds of the present invention will be described hereunder. The structural characteristic of the image forming compounds of the present invention resides in the coupling component comprising a 1H-pyrazolo[1,5-b][1,2,4]triazole skeleton nucleus. Said 1H-pyrazolo[1,5-b][1,2,4]triazole skeleton nucleus may be synthesized by means of various methods, and a method of the following route is advantageous among them, as being most suitable for the synthesis thereof.

A 5-aminopyrazole compound is first reacted with an imidate compound and then with a hydroxylamine to obtain an amidoxime compound, which is thereafter dehydrated and ring closed in the presence of the following compounds (1) and (2), as shown in the following reaction scheme.

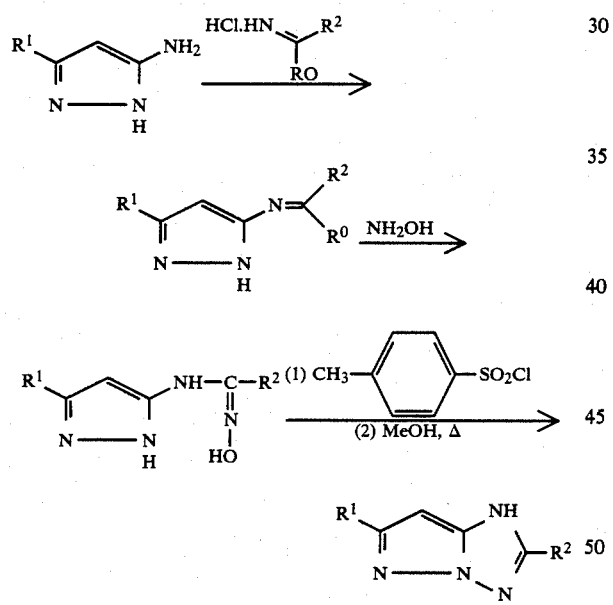

In the above reaction scheme, $R^1$ and $R^2$ may be the same or different and each represents a group selected from a hydrogen atom, a halogen atom, a hydroxyl group, a cyano group, a carboxyl group, or a substituted or unsubstituted alkyl, aralkyl, cycloalkyl, aryl, heterocyclic, alkoxy, aryloxy, amino, acylamino, sulfonylamino, acyl, sulfonyl, carbamoyl, sulfamoyl, ureido, alkylthio or arylthio group.

Next, the resulting compound is coupled with a pertinent aniline-sulfonic acid compound, and then the sulfo group in the formed compound is converted into a sulfonyl chloride and condensed with a component of a substrate component Y, at least to obtain the aimed image forming compound where groups Dye and X are bonded via a group $R^3$.

In the case when an imidate compound having a sulfo group in the group $R^2$ is used, an image forming compound where groups Dye and X are bonded via the group $R^2$ may be obtained.

Apart from the above method, a Y-X compound having a terminal amino group may be used, which is first diazotized and then coupled with a 1H-pyrazolo[1,5-b][1,2,4]triazole compound for formation of the image forming compound of the present invention.

Some concrete examples for synthesis of the present compounds are given hereunder.

Synthesis of Image Forming Compound (7)

Step (1):

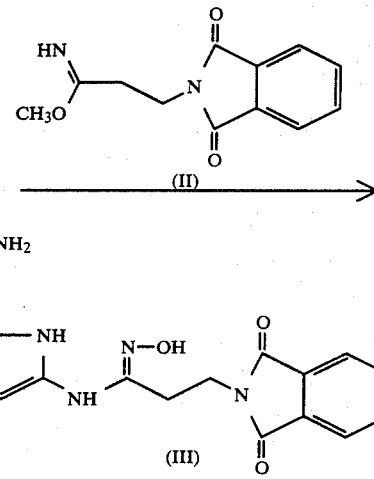

218 g (2.2 mols) of 3-methyl-5-aminopyrazole (I) was dissolved in 3.2 liters of water and stirred at room temperature. Next, 548 g (2.04 mols) of imido ester hydrochloride (II) was added thereto at one time and stirred, whereby a crystal gradually precipitated out. After stirring for 1 hour, a hydroxylamine aqueous solution (prepared by blending 156 g of hydroxylamine hydrochloride and 155 g of potassium carbonate in 1 liter of water) was added thereto and further stirred, whereby a crystal of an amidoxime (III) gradually precipitated out. The formed crystal was taken out by filtration, washed with water and dried. Yield: 490 g (77%), m.p.: 200°-202° C.

Step (2):

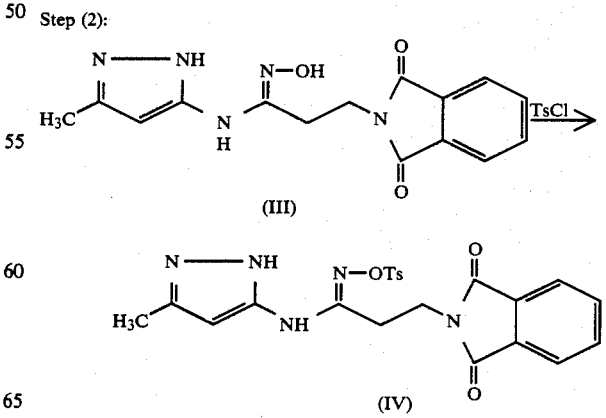

490 g (1.56 mols) of amidoxime (III) was added to 1.5 liters of acetonitrile and then a solution prepared by dissolving 256 g (1.34 mols) of p-toluenesulfonyl chloride (TsCl) in 800 ml of acetonitrile was added dropwise thereto at room temperature while stirring. After the addition, the whole was stirred for 30 minutes, and then 110 ml (1.36 mols) of pyridine was added dropwise thereto. The resulting reaction solution was poured into 4 liters of ice water and stirred, and the precipitated crystal (IV) was taken out by filtration. Yield: 706 g (97%). m.p.: 128°–129° C.

Step (3):

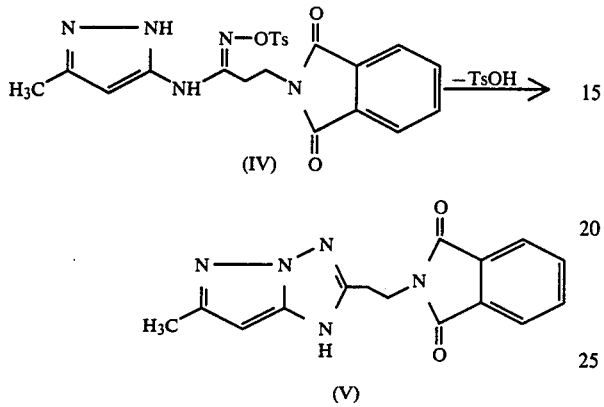

702 g of the above-obtained product (IV) was added to 5.6 liters of methanol and heated under reflux. After 2 hours, methanol was distilled out from the reaction solution under reduced pressure, and the remaining residue was poured into 6 liters of water. The resulting solution was neutralized with sodium hydrogencarbonate and the precipitated crystal was taken out by filtration, which was washed with ethyl acetate and dried to obtain 309 g of compound (V).

Yield: 70%, m.p.: ~230° C. (decomposition).

Step (4):

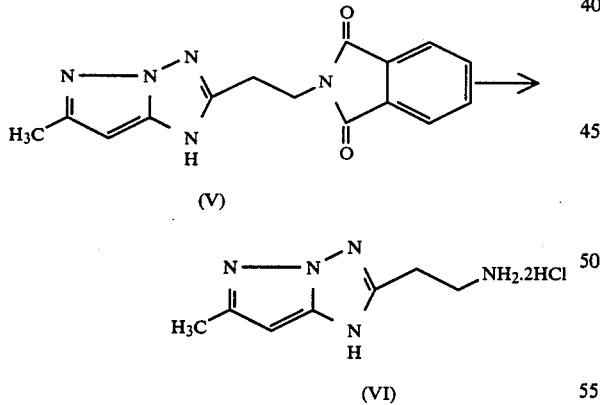

54 g of 89% hydrazine hydrate (1.05 mols) was added to a mixture of 1.5 liters of methanol and 259 g (0.877 mol) of the compound (V) at room temperature. After the whole was heated under reflux for 6 hours, the resulting reaction solution was cooled to room temperature, and then 800 ml of water was added thereto and the solution was adjusted to have a pH value of 2, with a concentrated hydrochloric acid. A crystal of phthalhydrazide was taken out by filtration and washed with water, and the filtrate was concentrated under reduced pressure to obtain a crude crystal of the compound (VI). Methanol was added to the obtained crude crystal and the crystal was finely pulverized and filtered to obtain a colorless powder crystal of the compound (VI). Yield: 125 g (60%). m.p.: 200°–265° C. (decomposition).

Step (5):

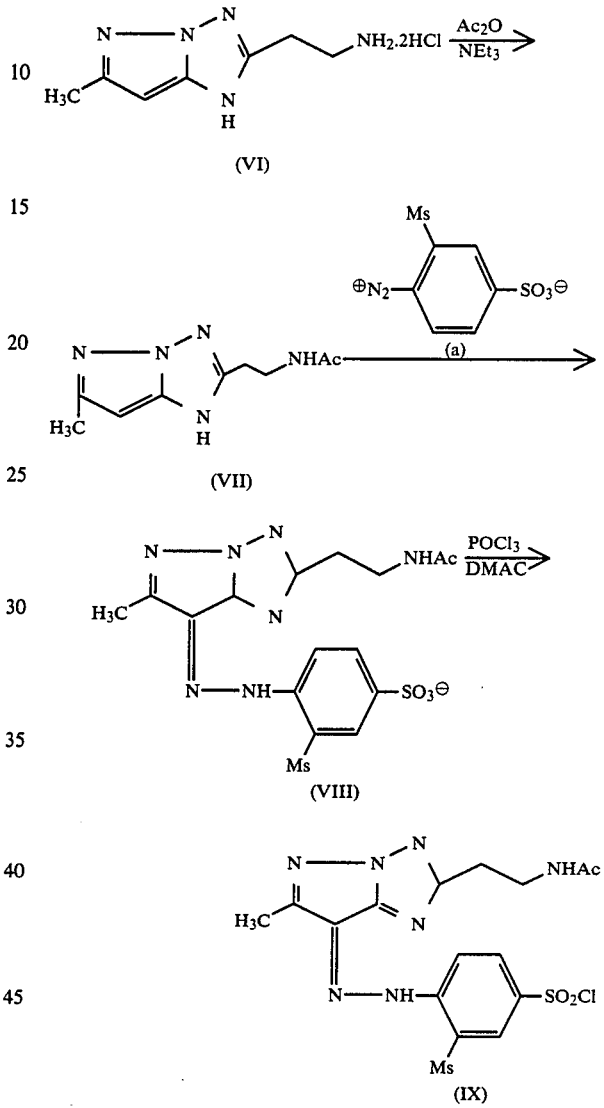

12 g of acetic anhydride was added dropwise to a mixture of 23.8 g of the compound (VI), 22 g of triethylamine (NEt₃) and 150 ml of acetonitrile at room temperature. Afterwards, the temperature of the resulting mixture was elevated up to 60° C. and then the whole was heated and stirred at 60° to 65° C. for 30 minutes. While hot, 100 ml of water was added thereto, and the resulting solution was left cooled to room temperature to obtain a coupling solution. On the other hand, 32.4 g of calcium 2-methanesulfonylaniline-4-sulfonate was diazotized with nitrosylsulfuric acid in a conventional manner.

The above-prepared coupling component solution was cooled to 0° C. and then said diazo solution (a) was added thereto little by little at 0° to 5° C. In addition, sodium acetate was added thereto at 5° to 10° C. whereby the pH value of the solution was adjusted to 5.

48.3 g of tetrabutylammonium bromide was added to the resulting solution, which was then extracted with ethyl acetate. The solvent was distilled out from the extract under reduced pressure, and 100 ml of acetanilide and 30 ml of dimethylacetamide (DMAc) were added to the resulting residue, and 30 ml of phosphorus oxychloride was added dropwise thereto at 15° to 20° C. The reaction mixture was stirred for 2 hours at 40° to 45° C. and then poured into an ice water. The thus formed yellow precipitate was taken out by filtration, washed with water and dried with an air to obtain the compound (IX).

method or a noble metal sensitization method may be carried out singly or in the form of a combination of said methods, which are known in the art of an emulsion for a conventional light-sensitive material.

Silver halide emulsions which may be used in the present invention may either be surface latent image type emulsions where a latent image is mainly formed on the surface of particles or internal latent image type emulsions where a latent image is mainly formed in the inner part of particles. A direct reversal emulsion comprising a combination of an internal latent image type emulsion and a nucleus forming agent may also be used Step (6):

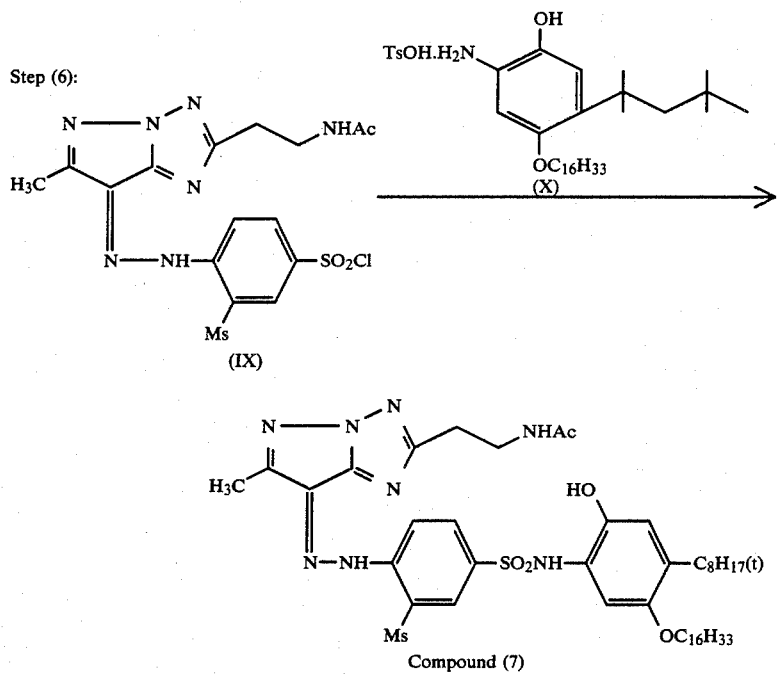

Compound (7)

11.7 g of the above obtained compound (IX) was added little by little to a mixture of 15 g of 2-amino-4-hexadecyloxy-5-(1,1,3,3-tetramethylbutyl)phenol p-toluensulfonate (X), 15 ml of pyridine and 80 ml of dimethylacetamide, while nitrogen was was blown thereinto. The whole was stirred for 1 hour at room temperature, and then the reaction solution was poured into a cold dilute hydrochloric acid solution to obtain a precipitate, which was then extracted with ethyl acetate. The ethyl acetate layer was isolated, washed with water and dried, and then the solvent was distilled out under reduced pressure. The resulting residue was purified by column chromatography (eluent: ethyl acetate/-hexane of 1/1) to obtain a yellow crystal of the yellow image forming compound (7). Yield: 1.5 g (51%). m.p.: 198°–205° C. $\lambda_{max}$: 458 mm, $\epsilon = 3.5 \times 10^4$ (solvent: dimethylformamide).

Silver halides which may be used as a light-sensitive silver salt to be incorporated in the color light-sensitive materials of the present invention may be prepared by a method as described in U.S. Pat. No. 4,500,626. The present color light-sensitive materials may contain additives as described in said U.S. patent and silver halides having characteristics as described in said U.S. patent may be used in the present invention. A silver halide emulsion may be used, as being not post ripened, in the present invention and, in general, said emulsion is preferably used as being chemically sensitized. For instance, a sulfur sensitization method, a reduction sensitization in the present invention.

The amount of the light-sensitive silver halide to be coated on a support in the present invention is within the range of 1 mg to 10 g/m², as calculated in terms of the coated silver amount.

In the present invention, an organic metal salt which is relatively stable to light, especially an organic silver salt, is preferably used as an oxidizing agent, together with the photographic silver halide.

Details of said organic silver salts which may be used in the present invention are described in U.S. Pat. No. 4,500,626.

The silver halides to be used in the present invention may be spectrally sensitized with a methine dye or the like.

Details of said dyes are described in U.S. Pat. No. 4,500,626.

The photographic materials of the present invention may contain a reducing agent. As said reducing agent, those which are known in this technical field or color image forming compounds having a reductivity, which are described hereinafter, are preferred.

Examples of reducing agents which may be used in the present invention are described in U.S. Pat. No. 4,500,626.

The color light-sensitive materials of the present invention may contain, in addition to the yellow color image forming compound of the formula (I), any known magenta and/or cyan color image forming compounds and any other known yellow color image forming compounds, so far as said additional image forming compounds do not badly affect the photographic materials of the present invention, whereby color images of a broad range in a chromaticity diagram may be obtained. Accordingly, the color light-sensitive materials of the present invention may have at least three light-sensitive silver salt layers each having sensitivity in different spectral ranges.

Typical combinations comprising at least three light-sensitive silver salt emulsion layers each having sensitivity in different spectral ranges, as mentioned above, are described in U.S. Pat. No. 4,500,626.

The photographic materials of the present invention may contain, if necessary, two or more emulsion layers having sensitivity in the same spectral range, which are distinguished in accordance with the sensitivity of said emulsion.

The above-mentioned color image forming compounds are added to the above-mentioned light-sensitive silver salt emulsion layer and/or a light-insensitive hydrophilic colloid layer which is adjacent to said light-sensitive silver salt emulsion layer. For said addition, said image forming compounds may be incorporated in the light-sensitive materials together with other photographic additives, by means of a known method, e.g., as described in U.S. Pat. No. 2,322,027. In this case, conventional high boiling point organic solvents, low boiling point organic solvents or other various kinds of surfactants, etc., may be used. The amount of the organic solvent to be used in the present invention is 10 g or less, preferably 5 g or less, on the basis of 1 g of the image forming compound used.

The color light-sensitive materials of the present invention have photographic elements comprising a light-sensitive element capable of forming or releasing a dye by development to form a color image and, if necessary, a dye fixing element for fixation of the dye formed. In particular, in such a system as forming an image by diffusion transfer of a dye, said light-sensitive element and dye fixing element are essential, and two embodiments are typical, one being attained by separately coating said light-sensitive element and dye fixing element on two different supports, individually, and the other being attained by coating both of said two elements on the same support together.

The system for development of the light-sensitive materials of the present invention is not specifically limited, and in particular, a heat development system is preferred in the present invention.

In the heat development system, the yellow image forming compounds of the formula (I) of the present invention may form or release a movable yellow dye, when a light-sensitive silver salt is reduced into silver under a high temperature condition, in accordance with or reversely in accordance with said reaction, and the light-sensitive materials of the present invention may contain the above-mentioned known dye forming substances of magenta and/or cyan image forming compounds or known yellow color forming substances, together with said compounds of the formula (I).

Color image forming compounds or dye forming substances, which may be co-used in the photographic materials of the present invention, include, for example, couplers capable of being reacted with a developing agent. In the system where a coupler is used, an oxidized form of a developing agent yielded by an oxidation reduction reaction of a silver salt and said developing agent reacts with the coupler, to form a dye, which is described in numerous well known publications. Examples of developing agents and couplers are described in detail in *The Theory of the Photographic Process* (written by T. H. James), 4th Ed., pp. 291-334 and pp. 354-361, and *Photographic Chemistry* (written by Shinichi Kikuchi and published by Kyoritsu Shuppan Publishing Co.), 4th Ed., pp. 284-295.

Silver-dye compounds comprising a combination of an organic silver salt and a dye may be examples of said dye forming substances. Concrete examples of said silver-dye compounds are described in *Research Disclosure* (May, 1978), RD No. 16966, etc.

Azo dyes which may be used in a heat development silver-dye bleaching method may be examples of said dye forming substances. Concrete examples of said azo dyes and said bleaching method are described in U.S. Pat. No. 4,235,957 and *Research Disclosure* (April, 1976), RD No. 14433, etc.

In addition, leuco dyes as described, e.g., in U.S. Pat. Nos. 3,985,565 and 4,022,617 may be examples of said dye forming substances.

Other examples of said dye forming substances include compounds having a function capable of imagewise releasing and diffusing a diffusible dye.

Said compounds may be represented by the formula (LI):

$$(Dye'-X')_n-Y' \qquad (LI)$$

wherein Dye' represents a dye residue or a precursor residue thereof represented by formula (II), or represents a known dye residue or a precursor residue thereof; X' represents a bond or a binding group; Y' represents a group capable of yielding a difference of diffusibility of a compound of said formula (Dye'—X-')$_n$—Y', corresponding to or reversely corresponding to a photographic silver salt imagewise having a latent image, or alternatively represents a group capable of releasing said Dye' and yielding a difference of diffusibility between said Dye' released and a compound of said formula (Dye'—X')$_n$—Y'; n is an integer of 1 or 2; and when n is 2, two (Dye'—X')'s may be the same or different.

Various examples of the dye forming substances of the formula (LI) are disclosed in various patent specifications. For instance, U.S. Pat. Nos. 3,134,764, 3,362,819, 3,597,200, 3,544,545 and 3,482,972 describe color developers comprising a combination of a hydroquinone type developing agent and a dye component; Japanese Patent Application (OPI) No. 63618/76 describes such substances that may release a diffusible dye by an intramolecular nucleophilic substitution reaction; and Japanese Patent Application (OPI) No. 111628/74 describes such substances that may release a diffusible dye by an intramolecular rearrangement reaction of an isoxazolone ring. In all of said means, a diffusible dye is released or diffused in a non-developed part, but no dye is released or diffused in a developed part.

Apart from said means, another type of means has heretofore been proposed, where a dye releasing compound is previously converted into an oxidized form having no dye releasing ability and said oxidized compound is used together with a reducing agent or a precursor thereof, and, after development, said compound is reduced with said reducing agent, which has remained as not oxidized, thereby to release a diffusible dye from said compound. Examples of dye forming substances which may be used in said means are described, for example, in Japanese Patent Application (OPI) Nos. 110827/78, 130927/79, 164342/81 and 35533/78.

On the other hand, still other substances are known capable of releasing a diffusible dye in a developed part. For instance, British Patent No. 1,330,524, Japanese Patent Publication No. 39165/73 and U.S. Pat. No. 3,443,940 describe substances capable of releasing a diffusible dye by reaction of a coupler having a removable group of a diffusible dye and a developing agent in an oxidized form; and U.S. Pat. No. 3,227,550 describes substances capable of forming a diffusible dye by reaction of a coupler having a removable group of a nondiffusible group and a developing agent in an oxidized form.

However, said means using such color developing agents have a severe problem in that a formed image is often stained due to an oxidized and decomposed product of the developing agent used. In order to overcome said problem, therefore, some other dye releasing compounds which themselves have a reductivity and do not require any developing agent have heretofore been proposed.

Typical examples of said compounds are given in the following literature and publications. Definitions of general formulae therein are to be referred to those as described in the respective literature or publications. For instance, various kinds of dye forming substances as described in U.S. Pat. Nos. 3,928,312, 4,053,312, 4,055,428 and 4,336,322, Japanese Patent Application (OPI) Nos. 65839/84, 69839/84, 3819/78 and 104343/76, Research Disclosure, RD No. 17645, U.S. Pat. Nos. 3,725,062, 3,728,113 and 3,443,939 and Japanese Patent Application (OPI) No. 116537/83 may be used in the present invention together with the present compound of the formula (I).

Concrete examples of dye forming substances which may be co-sued together with the dye forming substances of the formula (I) of the present invention are compounds as described in Japanese Patent Application (OPI) No. 84236/84, and in particular, Compounds (1) to (3), (10) to (13), (16) to (19), (28) to (30), (33), (35), (38) to (40), (42) to (64) as described in said patent publication are preferably used in the present invention. In addition, compounds as described in U.S. Pat. No. 4,500,626 are also useful.

Regarding the relation between the light-sensitive element and the dye fixing element, the relation between a support and said elements and the relation between a white reflective layer and said elements of the color photographic materials of the present invention, the contents in U.S. Pat. No. 4,500,626 may be applied to the present invention.

The light-sensitive elements may contain, in addition to the light-sensitive silver salt emulsion layer, if necessary, a protective layer, an intermediate layer, an antistatic layer, a curling preventing layer, a peeling layer, a matting layer or the like auxiliary layer. In coating of said layers on a support, the means as described in U.S. Pat. No. 4,500,626 may be applied thereto.

In particular, an organic or inorganic matting agent is generally incorporated into a protective layer for the purpose of prevention of adhesion. In addition, said protective layer may further contain a mordanting agent, a UV-absorbent, etc. The protective layer and intermediate layer may comprise two or more layers, individually.

The intermediate layer may contain a reducing agent for prevention of color stain, a UV-absorbent, a white pigment such as $TiO_2$, etc. Said white pigment may be added not only to the intermediate layer but also to an emulsion layer for the purpose of increasing the sensitivity thereof.

The dye fixing element contains at least one layer containing a mordanting agent, and in the case when a dye fixing layer is positioned in the outermost surface part of said element, an additional protective layer may be provided thereon, if necessary.

The dye fixing element which may be used in the present invention may have, in addition to the above-described layers, if necessary, a peeling layer, a matting agent layer, a curling preventing layer or the like auxiliary layer.

One or more of the above-described layers may further contain a base and/or a base precursor for acceleration of dye transference, a hydrophilic hot melting solvent, a discoloration inhibitor for inhibition of discoloration of dyes formed, a UV-absorbent, a vinyl compound dispersion for increment of dimensional stability, a fluorescent agent, etc.

Regarding the layer constitution, binder, additives, addition of mordanting agent and position of the above-described light-sensitive element and/or dye fixing element of the present invention, the technical contents as described in U.S. Pat. No. 4,500,626 may be applied to the case of the present invention.

Regarding the light source for imagewise exposure of the photographic materials of the present invention to record images thereon, a radiation including visible rays may be applied to the present materials, and for instance, light sources as described in U.S. Pat. No. 4,500,626 may be applied thereto.

The photographic materials of the present invention may contain an image forming accelerator. Image forming accelerators are those having various kinds of functions, for example, to accelerate the oxidation reduction reaction of a silver salt oxidizing agent and a reducing agent, to accelerate the formation of a dye from a dye forming substance or the decomposition of the dye formed or the release of a movable dye from a dye releasing substance, or to accelerate the transference of the dye formed from a light-sensitive element layer to a dye fixing element layer. From the viewpoint of the physicochemical functions of said accelerators, these may be classified into bases or base precursors, nucleophilic compounds, oils, hot melting solvent, surfactants and compounds having a mutual reactivity with silver or silver ion. In this connection, it is to be noted that said accelerator substances have in general composite functions and have two or more accelerating functions as mentioned above.

Details of said image forming accelerators are described in U.S. Pat. No. 4,500,626.

Various kinds of development stopping agents may be used for the light-sensitive materials of the present invention for the purpose of obtaining at any time constant images relative to the variation of the treatment temperature and treatment time during development.

Development stopping agents used herein are compounds which may neutralize a base or may react therewith immediately after a proper development of the light-sensitive material, to lower the concentration of the base existing in the photographic layer thereby to stop the development of said material, or compounds which may mutually react with a silver or a silver salt immediately after a proper development, thereby to stop the development.

The light-sensitive materials of the present invention may further contain a compound which may activate the development and at the same time may stabilize the image formed.

The light-sensitive materials of the present invention may contain, if necessary, an image toning agent. Examples of effective toning agents which may be used in the present invention are described in U.S. Pat. No. 4,500,626.

The binder to be used in the light-sensitive element or in the dye fixing element of the light-sensitive materials of the present invention may be used singly or in the form of a mixture of two or more kinds of binders. Said binders are preferably hydrophilic. In particular, transparent or semitransparent hydrophilic binders are typical, for example, including natural substances such as proteins, e.g., gelatin, gelatin derivatives or cellulose derivatives, and polysaccharides such as starch or gum arabic; and synthetic polymer substances such as water-soluble polyvinyl compounds, e.g., polyvinylpyrrolidone or acrylamide polymer, etc. In addition, other synthetic polymer substances may also be used for said binder, such as a dispersive vinyl compound in the form of a latex, which may especially increase the dimensional stability of photographic materials.

The amount of the binder to be coated is 20 g/m$^2$ or less, preferably 10 g/m$^2$ or less, more preferably 7 g/m$^2$ or less.

The ratio of a high boiling point organic solvent to be dispersed in said binder together with a hydrophobic compound such as a dye forming substance to the binder is suitably 1 cc or less (of said solvent) to 1 g (of the binder), preferably 0.5 cc or less (of the solvent), more preferably 0.3 cc or less (of the solvent), to 1 g (of the binder).

Supports which may be used for the light-sensitive element and the dye fixing element in the light-sensitive materials of the present invention, the latter dye fixing element being optional in the present materials, are those which may be resistant to the treatment temperature, in the case when the materials are treated in a heat development system. In general, not only glasses, papers, metals and the analogue substances but also various support materials as described in U.S. Pat. No. 4,500,626 may be used as supports in the present invention.

The light-sensitive materials of the present invention may contain a dye transferring assistant agent for accelerating the transference of the dye formed in the light-sensitive element from said element into the dye fixing element.

Said dye transferring assistant agent may be applied to the photographic material after ddvelopment, or alternatively may previously be incorporated thereinto before development. In the former system where said dye transferring assistant agent is added later, water or a basic aqueous solution containing an inorganic alkali metal salt such as sodium or potassium hydroxide or an organic base may be used. The bases which may be used in the present invention are those as described hereinbefore with respect to image forming accelerators. In addition, a low boiling point solvent such as methanol, N,N-dimethylformamide, acetone or diisobutyl ketone or a mixture solution comprising said low boiling point solvent and water or a basic aqueous solution may also be used. In order to add said dye transferring assistant agent, the dye fixing element and/or the light-sensitive element may be wetted with said assistant agent.

In the latter system where the dye transferring assistant agent is previously incorporated in the light-sensitive element and/or the dye fixing element, it is of course unnecessary to add later any further dye transferring assistant agent.

For application of the dye transferring assistant agent to the light-sensitive element and/or the dye fixing element, for example, the means as described in U.S. Pat. No. 4,500,626 may be used.

For the development of the light-sensitive element and/or the transference of the movable dye into the dye fixing element in the light-sensitive materials of the present invention, a heating means with a mere hot plate, an iron or a hot roller may be utilized. In particular, in the case when an electric heating means is utilized, a transparent or opaque heating element may be formed in a conventional manner known for manufacture of electric heating elements.

For manufacture of said electric heating elements, two means may be used, including a method where a membrane of an inorganic semiconductive material is used and another method where an organic membrane comprising a dispersion of electroconductive fine particles dispersed in a binder is used. For the manufacture of said elements in accordance with said means, materials as described in U.S. Pat. No. 4,500,626 may be used, and these materials are processed according to the direction, the means and the layer constitution as described in said U.S. patent. Regarding the mutual relation of the position of each of the heating element and the light-sensitive element, the matter as described in said U.S. patent may also be applied to the case of the present invention. Apart from said case, the electric heating element may be provided in a dye fixing element of the light-sensitive materials of the present invention.

In the case when the step for the heat development of the light-sensitive element and the step for the transference of the dye formed to the dye fixing elements are separately carried out in the light-sensitive materials of the present invention, the heating temperature in the heat development step for heating the light-sensitive material of the present invention is in the range of about 80° C. to about 250° C., and is especially preferably about 110° C. to about 180° C. On the other hand, the heating temperature in the transfer process for the transference of the dye formed in the light-sensitive material of the present invention is in the range of from the heating temperature in said heat development step to room temperature, and is especially preferably up to a temperature lower than the temperature in said heat development step by about 10° C.

The development and the transfer may be carried out at the same time or continuously, as described in detail in Japanese Patent Application (OPI) No. 218443/84, which is advantageous in the present invention. In this means, said image forming accelerator and/or dye transferring assistant agent may previously be incorporated in both or either the dye fixing element and/or the light-sensitive element, or alternatively, may be added later to said element(s). In said system where the development and the transference are carried out at the same time or continuously, the heating temperature is preferably 60° C. or higher, and preferably a temperature lower than the boiling point of the solvent used in the transference step. For instance, in the case when water is used as a solvent in transference, said temperature is preferably 60° C. to 100° C.

The present invention will now be explained in greater detail by reference to the following examples, which, however, are not intended to be interpreted as limiting the scope of the present invention.

Unless otherwise indicated, all percents, ratios, etc., are by weight.

EXAMPLE 1

A silver benzotriazole emulsions was prepared as follows:

28 g of gelatin and 13.2 g of benzotriazole were dissolved in 300 ml of water. The solution was kept at 40° C. and stirred. A solution of 17 g of silver nitrate dissolved in 100 ml of water was added to the above-prepared solution in the course of 2 minutes.

The pH value of this silver benzotriazole emulsion was regulated and sedimented to remove the excess salt therefrom. Afterwards, the pH value thereof was adjusted to 6.30 to obtain 400 g of the aimed silver benzotriazole emulsion.

A silver halide emulsion to be used in a fifth layer and a first layer was prepared as follows:

600 ml of an aqueous solution containing sodium chloride and potassium bromide and a silver nitrate aqueous solution (containing 0.59 mol of silver nitrate dissolved in 600 ml of water) were simultaneously added to a well stirred gelatin aqueous solution (containing 20 g of gelatin and 3 g of sodium chloride dissolved in 1,000 ml of water and warmed at 75° C.), in the course of 40 minutes at the same addition flow rate. Thus, a monodispersed cubic silver bromochloride emulsion (bromine content: 50 mol%) having an average grain size of 0.40 μm was obtained.

After washing with water and demineralizing, 5 mg of sodium thiosulfate and 20 mg of 4-hydroxy-6-methyl-1,3,3a,7-tetraazaindene were added to the obtained emulsion and heated at 60° C. for chemical sensitization thereof. The yield of the emulsion formed was 600 g.

Next, a silver halide emulsion for a third layer was prepared as follows:

600 ml of an aqueous solution containing sodium chloride and potassium bromide and a silver nitrate aqueous solution (containing 0.59 mol of silver nitrate dissolved in 600 ml of water) were simultaneously added to a well stirred gelatin aqueous solution (containing 20 g of gelatin and 3 g of sodium chloride dissolved in 1,000 ml of water and warmed at 75° C.), in the course of 40 minutes, at the same addition flow rate. Thus, a monodispersed cubic silver bromochloride emulsion (bromine content: 80 mol%) having an average grain size of 0.35 μm was obtained.

After washing with water and demineralizing, 5 mg of sodium thiosulfate and 20 mg of 4-hydroxy-6-methyl-1,3,3a,7-tetraazaindene were added to the obtained emulsion and heated at 60° C. for chemical sensitization thereof. The yield of the emulsion formed was 600 g.

Next, a gelatin dispersion of a color image forming substance was prepared as follows:

5 g of Yellow Image Forming Compound (3) (as given hereinbefore and included in the scope of the formula (I)), 0.5 g of 2-ethylhexyl succinate/sodium sulfonate (as surfactant) and 10 g of triisononyl phosphate were weighed, and 30 ml of ethyl acetate was added thereto and heated at about 60° C. and dissolved to obtain a uniform solution. The resultant solution was blended with 100 g of 10% solution of a lime-treated gelatin, while stirring, and then dispersed in a homogenizer for 10 minutes (10,000 rpm). The obtained dispersion refers to a yellow image forming compound dispersion.

In the same manner as mentioned above, with the exception that Magenta Image Forming Compound (A) (as given hereinafter) was used instead of Yellow Image Forming Compound (3) and that 7.5 g of tricresyl phosphate was used as a high boiling point solvent, a magenta image forming compound dispersion was obtained.

In addition, a cyan image forming compound dispersion was formed using Cyan Image Forming Compound (B) (as given hereinafter) in the same manner as mentioned above.

Using these materials, Color Photographic Material (A) composed of a multilayer constitution as shown in the following Table 1 was formed.

TABLE 1

| | |
|---|---|
| Sixth layer: | Gelatin (coated amount: 1,000 mg/m$^2$), |
| | Base precursor*$^3$ (coated amount: 600 mg/m$^2$), |
| | Silica*$^5$ (coated amount: 100 mg/m$^2$), |
| | Hardener*$^6$ (coated amount: 100 mg/m$^2$) |
| Fifth Layer: | Green Sensitive Emulsion Layer |
| | Silver bromochloride emulsion (bromide: 50 mol %, coated amount: silver-400 mg/m$^2$), |
| | Benzenesulfonamide (coated amount: 180 mg/m$^2$), |
| | Silver benzotriazole emulsion (coated amount: silver-100 mg/m$^2$), |
| | Sensitizer Dye (D-1) (coated amount: 10$^{-6}$ mol/m$^2$), |
| | Base precursor*$^3$ (coated amount: 390 mg/m$^2$), |
| | Yellow Image Forming Compound (3) (coated amount: 400 mg/m$^2$), |
| | Gelatin (coated amount: 1,000 mg/m$^2$), |
| | High boiling point solvent*$^4$ (coated amount: 800 mg/m$^2$), |
| | Surfactant*$^2$ (coated amount: 100 mg/m$^2$) |
| Fourth Layer: | Intermediate Layer |
| | Gelatin (coated amount: 1,200 mg/m$^2$), |
| | Base precursor*$^3$ (coated amount: 600 mg/m$^2$) |
| Third Layer: | Red-Sensitive Emulsion Layer |
| | Silver bromochloride emulsion (bromide: 80 mol %, coated amount: silver-300 mg/m$^2$), |
| | Benzenesulfonamide (coated amount: 180 mg/m$^2$), |
| | Silver benzotriazole emulsion (coated amount: silver-100 mg/m$^2$), |
| | Sensitizer Dye (D-2) (coated amount: 8 × 10$^{-7}$ mol/m$^2$), |
| | Base precursor*$^3$ (coated amount: 350 mg/m$^2$), |
| | Magenta Image Forming Compound (A) (coated amount: 400 mg/m$^2$), |
| | Gelatin (coated amount: 1,000 mg/m$^2$), |
| | High boiling point solvent*$^1$ (coated amount: 600 mg/m$^2$), |

TABLE 1-continued

| | |
|---|---|
| | Surfactant*2 (coated amount: 100 mg/m$^2$) |
| Second Layer: | Intermediate Layer |
| | Gelatin (coated amount: 1,000 mg/m$^2$), |
| | Base precursor*3 (coated amount: 600 mg/m$^2$) |
| First Layer: | Infrared Ray-Sensitive Emulsion Layer |
| | Silver bromochloride emulsion (bromide: 50 mol %, coated amount: silver-300 mg/m$^2$), |
| | Benzenesulfonamide (coated amount: 180 mg/m$^2$), |
| | Silver benzotriazole emulsion (coated amount: silver-100 mg/m$^2$), |
| | Sensitizer Dye (D-3) (coated amount: $10^{-8}$ mol/m$^2$), |
| | Base precursor*3 (coated amount: 390 mg/m$^2$), |
| | Cyan Image Forming Compound (B) (coated amount: 300 mg/m$^2$), |
| | Gelatin (coated amount: 1,000 mg/m$^2$), |
| | High boiling point solvent*4 (coated amount: 600 mg/m$^2$), |
| | Surfactant (coated amount: 100 mg/m$^2$) |

Support
*1: Tricresyl phosphate

*2: 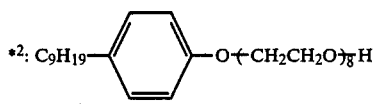

*3: 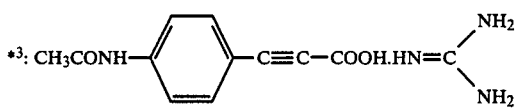

*4: (iso-$C_9H_{19}O)_3P=O$
*5: Particle size: 4 μm
*6: 1,2-Bis(vinylsulfonylacetamido)ethane Color Image Forming Compounds (A)

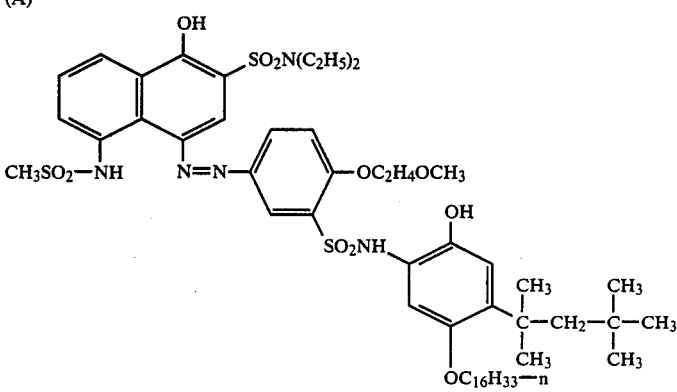

(B)

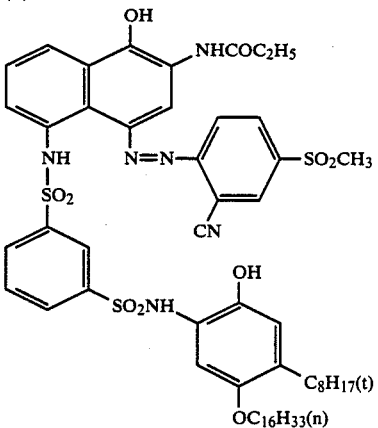

(C)

TABLE 1-continued

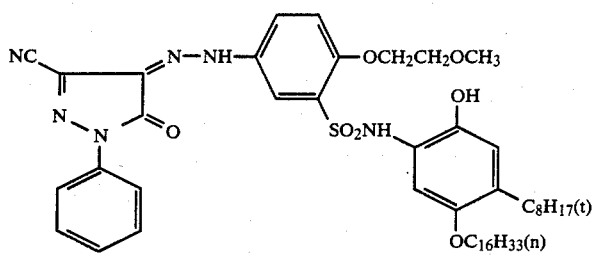

Sensitizer Dyes
(D-1)

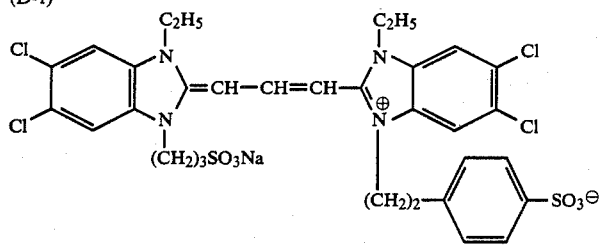

(D-2)

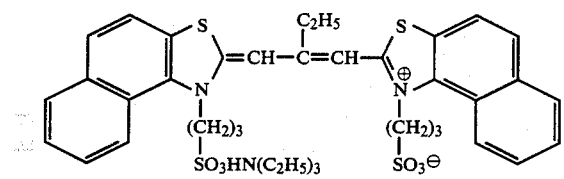

(D-3)

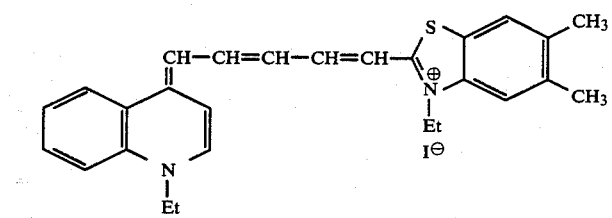

In the same manner as in the manufacture of Photographic Material (A), with the exception that the above-mentioned Yellow Image Forming Compound (C) or the above-mentioned Yellow Image Forming Compound (1), (2), (4), (7), (10) or (11) was used instead of Yellow Image Forming Compound (3), other Color Photographic Materials (B) through (H) were formed.

Next, a dye fixing material having a dye fixing layer was prepared as follows:

0.75 g of the following Gelatin Hardener (H-1), 0.25 g of the following Gelatin Hardener (H-2), 155 ml of water, 5 ml of 1% Surfactant (W-1) and 100 mg of 10% lime-treated gelatin were uniformly blended. The resulting mixture solution was uniformly coated on a paper support laminated with a titanium oxide-dispersed polyethylene to form a wet film layer having a thickness of 60 μm and then dried.

Gelatin Hardener (H-1):
$CH_2=CHSO_2CH_2CONHCH_2CH_2NHCOCH_2SO_2CH=CH_2$

Gelatin Hardener (H-2):
$CH_2=CHSO_2CH_2CONHCH_2CH_2CH_2NHCOCH_2SO_2CH=CH_2$

Surfactant (W-1):

-continued
$$CH_2-COOCH_2-CH(C_2H_5)C_4H_9$$
$$NaO_3S-CH-COOCH_2-CH(C_2H_4)C_4H_9$$

Next, 15 g of the following Polymer (I) and 5 g of the following Polymer (II) were dissolved in 180 ml of water, and the resulting solution was uniformly blended with 15 ml of 5% Surfactant (W-1) and 100 g of 10% lime-treated gelatin. The resulting mixture solution was uniformly coated on the previously coated film to form a wet film layer having a thickness of 85 μm. This was dried to form a dye fixing material.

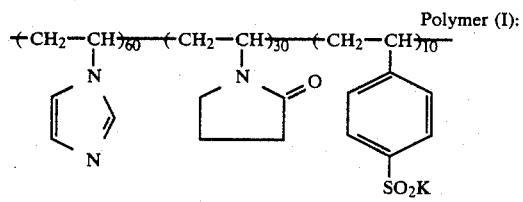

Polymer (I):

-continued

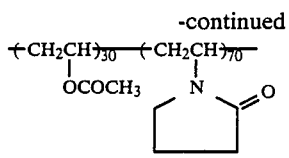  Polymer (II):

The color photographic material of multilayer constitution as obtained above was exposed to a tungsten lamp of 500 lux for 1 second, through a G-R-IR three-color separation filter composed of a 500–600 nm band pass filter for G, a 600–700 nm band pass filter for R and a filter to pass 700 nm or more for IR, the color density in said filter continuously varying.

After the exposure, the material was uniformly heated on a heat block heated at 140° C. for 30 seconds.

Next, water was applied to the surface of the layer of the dye fixing material in an amount of 15 ml/m² and the above light-sensitive material, after heat treatment, was put on said dye fixing material so that the surfaces of the coated film layer in each material faced to each other.

The thus adhered photographic material was heated on a heat block heated at 80° C. for 3 seconds or for 6 seconds, and then the dye fixing material was peeled off from the photographic material, whereby yellow, magenta and cyan images were formed on the fixing material, corresponding to the G-R-IR three-color separation filter, respectively.

Next, a transparent film having an ultraviolet absorbing layer was put on the surface of the film layer of the dye fixing material having said negative images, and a xenon ray (100,000 lux) was irradiated on the color images for 7 days. The density of the color images before and after irradiation of said xenon ray was measured, and the light fastness of the images formed was evaluated from the measured data. The following Table 2 shows the transferred density of yellow obtained in correspondence to a G filter and the dye retention percentage at a reflection density of 1.0.

TABLE 2

| Sample No. | Yellow Image Forming Compound | Maximum Density after Heated for 3 Seconds | Maximum Density after Heated for 6 Minutes | Dye Retention Percentage (%) | Note |
|---|---|---|---|---|---|
| (A) | (3) | 1.79 | 2.24 | 82 | Present Sample |
| (B) | (C) | 1.21 | 2.02 | 60 | Comparative Sample |
| (C) | (1) | 1.71 | 2.14 | 76 | Present Sample |
| (D) | (2) | 1.73 | 2.16 | 78 | Present Sample |
| (E) | (4) | 1.73 | 2.16 | 75 | Present Sample |
| (F) | (7) | 1.76 | 2.20 | 74 | Present Sample |
| (G) | (10) | 1.68 | 2.10 | 77 | Present Sample |
| (H) | (11) | 1.74 | 2.17 | 75 | Present Sample |

Dye retention percentage = $\dfrac{\text{Dye density after xenon irradiation for 7 days}}{\text{Dye density before xenon irradiation}} \times 100$ The above Table 2 proves the fact that the color photographic materials of the present invention each containing a yellow image forming compound falling within the scope of the formula (I) are superior to Comparative Sample (B) in that the yellow dye transference is better and the yellow image formed has better light fastness.

While the invention has been described in detail and with reference to specific embodiments thereof, it will be apparent to one skilled in the art that various changes and modifications can be made therein without departing from the spirit and scope thereof.

What is claimed is:

1. A color light-sensitive material having at least one image forming compound of the following formula (I) on a support $$(\text{Dye-X})_q\text{-Y} \qquad (I)$$

wherein Dye represents a yellow dye residue or a dye precursor residue represented by the following formula (II); X represents a bond or a binding group; Y represents a group capable of yielding a difference of diffusibility of a dye component before and after the reaction with a photographic silver salt imagewise having a latent image, corresponding to or reversely corresponding to said photographic silver salt; q is 1 or 2, and when q is 2, Dye-X may be the same or different;

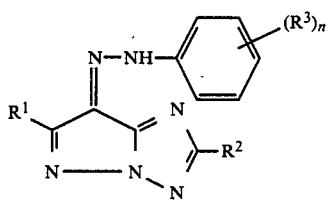  (II)

wherein R¹, R² and R³ may be the same or different and each represents a group selected from a hydrogen atom, a halogen atom, a hydroxyl group, a cyano group, a carboxyl group, or a substituted or unsubstituted alkyl, aralkyl, cycloalkyl, aryl, heterocyclic, alkoxy, aryloxy, amino, acylamino, sulfonylamino, acyl, sulfonyl, carbamoyl, sulfamoyl, ureido, alkylthio or arylthio group; n is an integer selected from 0 to 4, and when n is an integer of from 2 to 4, said R³ may be the same or different; Dye and X are bound to each other via any of said R¹, R² and R³ in the formula (II).

2. A color light-sensitive material as claimed in claim 1, wherein X in the formula (I) represents an —NR⁴— group (in which R⁴ represents a hydrogen atom, an alkyl group or a substituted alkyl group), an —SO₂— group, a —CO— group, an alkylene group, a substituted alkylene group, a phenylene group, a substituted phenylene group, a naphthylene group, a substituted naphthylene group, an —O— group, an —SO— group or a group formed by the combination of two or more of said groups.

3. A color light-sensitive material as claimed in claim 2, wherein X in the formula (I) represents —NR$^4$—SO$_2$—, —NR$^4$—CO— or —R$^5$-(-L-)$_k$(R$^6$)$_l$- in which R$^4$ represents a hydrogen atom, an alkyl group or a substituted alkyl group, R$^5$ and R$^6$ each represents an alkylene group, a substituted alkylene group, a phenylene group, a substituted phenylene group, a naphthylene group or a substituted naphthylene group, L represents —O—, —CO—, —SO—, —SO$_2$—, —SO$_2$NH—, —NHSO$_2$—, —CONH— or —NHCO—, k is 0 or 1, l is 1 when k=1, and l is 0 or 1 when k=0.

4. A color light-sensitive material as claimed in claim 3, wherein X in the formula (I) represents a combination of —NR$^4$—SO$_2$— and —NR$^4$—CO— or —R$^5$-(-L-)$_k$(R$^6$)$_l$-.

5. A color light-sensitive material as claimed in claim 1, wherein R$^1$ in the formula (II) represents a substituted or unsubstituted alkyl group having from 1 to 4 carbon atoms, a substituted or unsubstituted alkoxy group having from 1 to 4 carbon atoms, a substituted or unsubstituted aryl group having from 6 to 8 carbon atoms, a hydroxyl group, a cyano group, a carbamoyl group or a carboxyl group.

6. A color light-sensitive material as claimed in claim 1, wherein R$^2$ in the formula (II) represents a substituted or unsubstituted alkyl group having from 1 to 8 carbon atoms, a substituted or unsubstituted aryl group having from 6 to 8 carbon atoms, a substituted or unsubstituted aralkyl group having from 7 to 12 carbon atoms, a substituted or unsubstituted alkoxy group having from 1 to 6 carbon atoms, an acylamino group having from 2 to 8 carbon atoms or a sulfonylamino group having from 1 to 7 carbon atoms.

7. A color light-sensitive material as claimed in claim 1, wherein R$^3$ in the formula (II) represents a hydrogen atom, a halogen atom, a cyano group, a carboxyl group, a substituted or unsubstituted carbamoyl group having from 1 to 5 carbon atoms, a substituted or unsubstituted sulfamoyl group having from 0 to 4 carbon atoms, a substituted or unsubstituted sulfonyl group having from 1 to 4 carbon atoms, a methyl group, a methoxy group or a methoxyethoxy group.

8. A color light-sensitive material as claimed in claim 1, wherein Y in the formula (I) represents a group of the following formula (Y$_I$):

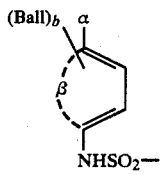

wherein $\beta$ represents a non-metallic atomic group necessary for formation of a benzene ring, which may be condensed with a carbon ring or a hetero ring; $\alpha$ represents —OG$^{11}$ or —NHG$^{12}$ (in which G$^{11}$ represents a hydrogen atom or a group capable of being hydrolyzed to form a hydroxyl group, and G$^{12}$ represents a hydrogen atom, an alkyl group having from 1 to 22 carbon atoms or a group which makes said NHG$^{12}$ hydrolyzable; Ball represents a ballast group; and b is 0, 1 or 2.

9. A color light-sensitive material as claimed in claim 1, wherein Y in the formula (I) represents a group of the following formula (Y$_{II}$):

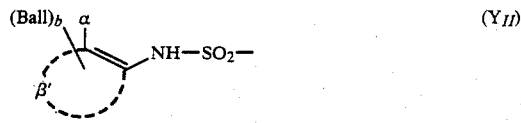

wherein Ball, $\alpha$ and b have the same meanings as in the formula (Y$_I$) in claim 8; and $\beta'$ represents an atomic group necessary for formation of a carbon ring, which may further be condensed with a carbon ring or a hetero ring.

10. A color light-sensitive material as claimed in claim 1, wherein Y in the formula (I) represents a group of the following formula (Y$_{III}$):

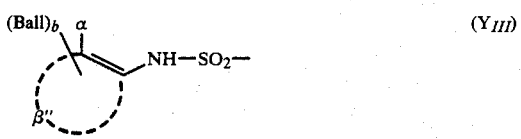

wherein Ball, $\alpha$ and b have the same meanings as in the formula (Y$_I$) in claim 8; and $\beta''$ represents an atomic group necessary for formation of a hetero ring which may further be condensed with a carbon ring or a hetero ring.

11. A color light-sensitive material as claimed in claim 1, wherein Y in the formula (I) represents a group of the following formula (Y$_{IV}$):

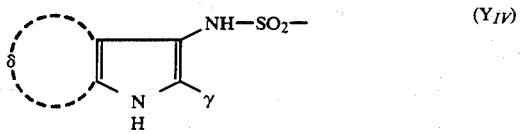

wherein $\gamma$ represents a hydrogen atom or a substituted or unsubstituted alkyl, aryl or heterocyclic group, or a group of —CO—G$^{21}$, G$^{21}$ represents a group of

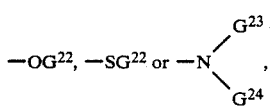

G$^{22}$ represents a hydrogen atom, an alkyl group, a cycloalkyl group or an aryl group, G$^{23}$ represents the same group as G$^{22}$ or represents an acyl group derived from an aliphatic or aromatic carboxylic acid or a sulfonic acid, G$^{24}$ represents a hydrogen atom or a substituted or unsubstituted alkyl group; and $\delta$ represents a residue necessary for completing a condensed benzene ring.

12. A color light-sensitive material as claimed in claim 1, wherein Y in the formula (I) represents a group of the following formula (Y$_V$):

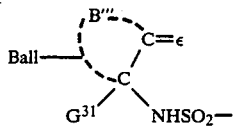
(Y$_V$)

wherein Ball has the same meaning as in the formula (Y$_I$) in claim 8; ε represents an oxygen atom or =NG$^{32}$ (where G$^{32}$ represents a hydroxyl group or an optionally substituted amino group); β''' represents an atomic group necessary for formation of a 5-, 6- or 7-membered, saturated or unsaturated nonaromatic hydrocarbon ring; and G$^{31}$ represents a hydrogen atom or a halogen atom.

13. A color light-sensitive material as claimed in claim 1, wherein Y in the formula (I) represents a group of the following formula (Y$_{VI}$):

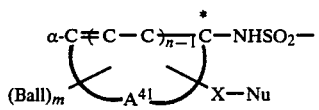
(Y$_{VI}$)

wherein α represents OR$^{41}$ or NHR$^{42}$, R$^{41}$ represents a hydrogen atom or a hydrolyzable component residue, R$^{42}$ represents a hydrogen atom or a alkyl group having from 1 to 50 carbon atoms or represents a group which makes NHR$^{42}$ hydrolyzable; A$^{41}$ represents an atomic group necessary for formation of an aromatic ring; Ball represents an organic group which may keep the compound in a passive state, as existing in an aromatic ring, and plural Ball's may be the same or different; m in an integer of 1 or 2; X represents a divalent organic group having from 1 to 8 carbon atoms; a nucleophilic group (Nu) and an electrophilic center (asterisked carbon, C*) formed by oxidation form a 5-membered to 12-membered ring; Nu represents a nucleophilic group; and n is an integer of 1 or 2.

14. A color light-sensitive material as claimed in claim 1, wherein Y in the formula (I) represents a group of the following formula (Y$_{VII}$):

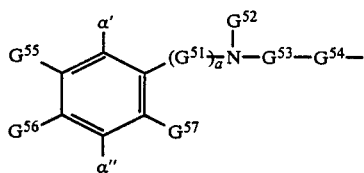
(Y$_{VII}$)

wherein α' represents an oxidizable nucleophilic group or a precursor thereof; α'' represents a dialkylamino group or may be any group as defined in α'; G$^{51}$ represents an alkylene group having from 1 to 3 carbon atoms; a is 0 or 1; G$^{52}$ represents a substituted or unsubstituted alkyl group having from 1 to 40 carbon atoms or a substituted or unsubstituted aryl group having from 6 to 40 carbon atoms; G$^{53}$ represents an electrophilic group; G$^{54}$ represents an oxygen atom, a sulfur atom, a selenium atom or a nitrogen atom, and when this is a nitrogen atom, said nitrogen atom may be substituted by a hydrogen atom, an alkyl group or a substituted alkyl group having from 1 to 10 carbon atoms or an aromatic residue having from 6 to 20 carbon atoms; G$^{55}$, G$^{56}$ and G$^{57}$ each represents a hydrogen atom, a halogen atom, a carbonyl group, a sulfamyl group, a sulfonamido group or an alkyloxy group having from 1 to 40 carbon atoms, or may have the same meaning as the group G$^{52}$; G$^{55}$ and G$^{56}$ may together form a 5- to 7-membered ring; or G$^{56}$ may represent a group

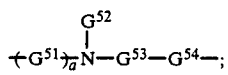

and with the proviso that at least one of G$^{52}$, G$^{55}$, G$^{56}$ and G$^{57}$ must represent a ballast group.

15. A color light-sensitive material as claimed in claim 1, wherein Y in the formula (I) represents a group of the following formula (Y$_{VIII}$) or (Y$_{IX}$):

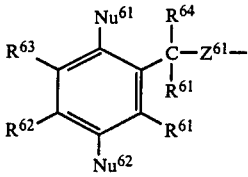
(Y$_{VIII}$)

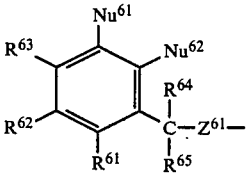
(Y$_{IX}$)

wherein Nu$^{61}$ and Nu$^{62}$ may be the same or different and each represents a nucleophilic group or a precursor thereof; Z$^{61}$ represents a divalent atomic group which is electrically negative to the carbon atom substituted by groups R$^{64}$ and R$^{65}$; R$^{61}$, R$^{62}$ and R$^{63}$ each represents a hydrogen atom, a halogen atom, an alkyl group, an alkoxy group or an acylamino group; or R$^{61}$ and R$^{62}$ may form a condensed ring, when positioned in the adjacent positions on the ring, together with the remaining atoms of the molecule; or said R$^{62}$ and R$^{63}$ may form a condensed ring together with the remaining atoms of the molecule; and R$^{64}$ and R$^{65}$ may be the same or different and each represents a hydrogen atom, a hydrocarbon residue or a substituted hydrocarbon residue; with the proviso that at least one of substituents R$^{61}$, R$^{62}$, R$^{63}$, R$^{64}$ and R$^{65}$ must contain a ballast group (Ball) of a sufficiently large size so that the compound may be kept immobile.

16. A color light-sensitive material as claimed in claim 1, wherein Y in the formula (I) represents a group of the following formula (Y$_X$):

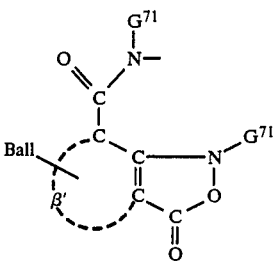
(Y$_X$)

wherein Ball and β' have the same meanings as in the formula (Y$_{II}$) in claim 9; and G$^{71}$ represents an alkyl group or a substituted alkyl group.

17. A color light-sensitive material as claimed in claim 1, wherein Y in the formula (I) represents a group of the following formula ($Y_{XI}$):

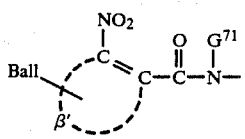 ($Y_{XI}$)

wherein Ball and $\beta'$ have the same meanings as in the formula ($Y_{II}$) in claim 9; and $G^{71}$ represents an alkyl group or a substituted alkyl group.

18. A color light-sensitive material as claimed in claim 1, wherein Y in the formula (I) represents a group of the following formula ($Y_{XII}$):

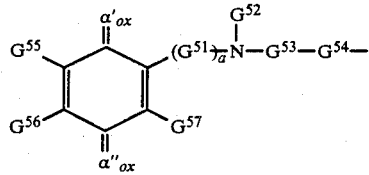 ($Y_{XII}$)

wherein $\alpha'_{ox}$ and $\alpha''_{ox}$ each represents a group capable of yielding a group of $\alpha'$ or $\alpha''$, respectively, by reduction; and $\alpha'$, $\alpha''$, $G^{51}$, $G^{52}$, $G^{53}$, $G^{54}$, $G^{55}$, $G^{56}$, $G^{57}$ and a have the same meanings as in the formula ($Y_{VII}$) in claim 14.

19. A color light-sensitive material as claimed in claim 1, wherein Y in the formula (I) represents a group of the following formula ($Y_{XIIIA}$) or ($Y_{XIIIB}$):

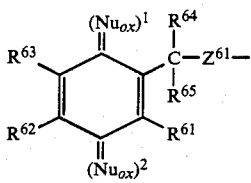 ($Y_{XIIIA}$)

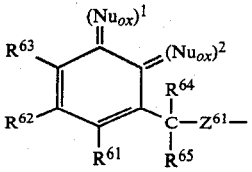 ($Y_{XIIIB}$)

wherein $(Nu_{ox})^1$ and $(Nu_{ox})^2$ may be the same or different and each represents an oxidized nucleophilic group; and the other symbols have the same meanings as in the formulae ($Y_{VIII}$) or ($Y_{IX}$) in claim 15.

20. A color light-sensitive material as claimed in claim 1, wherein Y in the formula (I) represents a group of the following formula ($Y_{XIV}$):

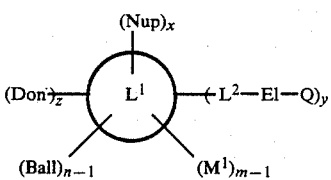 ($Y_{XIV}$)

wherein n, x, y and z each are 1 or 2; m is an integer of 1 or more; Don represents an electron donor or a precursor-containing residue; $L^1$ represents an organic group for binding said Nup and —$L^2$—El—Q or Don; Nup represents a precursor of a nucleophilic group; El represents an electrophilic center; Q represents a divalent group; Ball represents a ballast group; $L^2$ represents a binding group; and $M^1$ represents a substituent.

* * * * *